(12) United States Patent
Moltzen et al.

(10) Patent No.: US 6,391,882 B1
(45) Date of Patent: May 21, 2002

(54) 4,5,6 AND 7-INDOLE AND INDOLINE DERIVATITIVES, THEIR PREPARATION AND USE

(75) Inventors: Ejner Knud Moltzen, Gentofte; Ivan Mikkelsen, Køge; Christian Korg-Jensen, Copenhagen, all of (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/719,849

(22) PCT Filed: Jun. 14, 1999

(86) PCT No.: PCT/DK99/00326

§ 371 Date: Feb. 1, 2001

§ 102(e) Date: Feb. 1, 2001

(87) PCT Pub. No.: WO99/67237

PCT Pub. Date: Dec. 17, 1999

(30) Foreign Application Priority Data

Jun. 19, 1998 (DK) .......................................... 1998 00820

(51) Int. Cl.[7] .................. A61K 31/495; C07D 413/00; C07D 421/00
(52) U.S. Cl. ..................... 514/254.04; 514/254.01; 514/254.02; 514/254.03; 514/326; 544/368; 544/373; 544/375; 544/376; 546/196; 546/197; 546/198; 546/199; 546/201
(58) Field of Search .............. 514/254.01, 254.02, 514/254.03, 254.04, 326; 544/368, 373, 375, 376; 546/196, 197, 198, 199, 201

(56) References Cited

U.S. PATENT DOCUMENTS 5,693,655 A  12/1997  Bottcher et al. ............ 514/323

FOREIGN PATENT DOCUMENTS

| DE | 4414113 A1 | 10/1995 |
| WO | 9421626 A1 | 9/1994 |
| WO | 95/33721 | * 12/1995 |
| WO | 9828293 A1 | 7/1998 |

OTHER PUBLICATIONS

European Journal of Pharmacology—Molecular Pharmacology Section, vol. 244, 1993, pp. 251–257, P. Schoeffter, "SDZ 216–525, a selective and potent 5–HT1A recptor antagonist".
Pharamcology Biochemistry and Behavior, vol. 46, 1993, pp 873–880, R. Bell, "Effects of (–)–Pindolol and SDZ 216–525 on Social and Agonistic Behavior in Mice".

* cited by examiner

Primary Examiner—Richard L. Raymond
Assistant Examiner—Tamthom N. Truong
(74) Attorney, Agent, or Firm—Darby & Darby

(57) ABSTRACT

A substituted 4-, 5-, 6-, and 7-indole derivative of Formula (I)

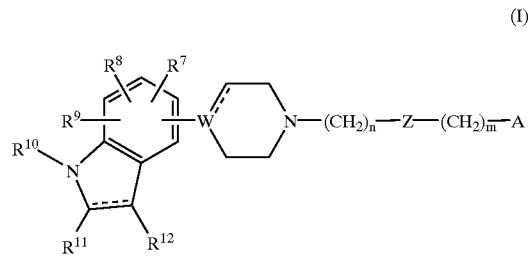

wherein A is a group having formula (IIA), (IIB), (IIC)

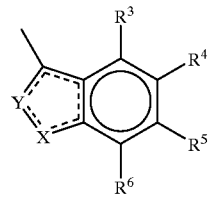

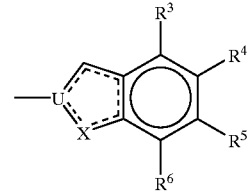

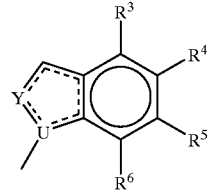

wherein X, U, Y, $R^3$ to $R^{12}$, Z, W, n and m are as defined above. The compounds are potent serotonin reuptake inhibitors and have $5\text{-HT}_{1A}$ receptor antagonistic activity.

14 Claims, No Drawings

4,5,6 AND 7-INDOLE AND INDOLINE DERIVATITIVES, THEIR PREPARATION AND USE

The present invention relates to novel 4, 5, 6 and 7-indole and indoline derivatives which are potent serotonin reuptake inhibitors, pharmaceutical compositions containing these compounds and the use thereof for the treatment of disorders or diseases responsive to the inhibition of serotonin re-uptake. The compounds of the invention also possess antagonistic activity at $5\text{-}HT_{1A}$ receptors and are considered to be particularly useful for the treatment of depression.

BACKGROUND

Selective serotonin (or 5-HT) reuptake inhibitors (SSRI's) such as fluoxetine, paroxetine, sertraline, fluvoxamine and citalopram represent a major step forward in the treatment of depression because they have fewer and less severe side effects compared to first generation antidepressant (tricyclics and non-selective MAO inhibitors). The side effects associated with first generation antidepressants are such that they cause some patients to withdraw from treatment.

SSRI's and all other antidepressants currently available suffer from a serious drawback in that several weeks of treatment is necessary to produce the therapeutic effect. The late onset of action is a significant problem, particularly in the treatment of patients with severe depression and suicide potential. Further, one in three patients are not responsive to SSRI's.

Electrophysiological experiments in rats have shown that acute administration of SSRI's reduces firing of 5-HT neurons of dorsal raphe nucleus in the rodent brain, whereas sustained treatment with SSRI's leads to normalization of the firing activity of the 5-HT neurons (Arborelius, L. et al, *Naunyn-Schmiedeberg's Arch. Pharmacol.* 1995, 352, 157; Gartside, S. E. et al, *Br. J. Pharmacol.* 1995, 115, 1064; Chaput, Y. et al, *Naunyn-Schmiedeberg's Arch. Pharmacol.* 1986, 33, 342).

Further, it has been shown that the recovery of the firing activity of 5-HT neurons is linked to desensitization of somatodendritic $5\text{-}HT_{1A}$ autoreceptors (Le Poul, E. et al, *Naunyn-Schmiedeberg's Arch. Pharmacol.* 1995, 352, 141; Invemizzi, R. et al, *Eur. J. Pharmacol.* 1994, 260, 243).

It has thus been suggested that simultaneous administration of SSRJ's and an agent causing rapid desensitization or inhibition of the $5\text{-}HT_{1A}$ receptor mediated feed back mechanism would lead to rapid onset of antidepressive effect (Artigas, F. et al, *Trends Neurosci.* 1996, 19, 378; De Vry, J., et al, *Drug News Perspec.* 1996, 9, 270).

The effect of combined administration of a compound that inhibits serotonin reuptake and a $5\text{-}HT_{1A}$ receptor antagonist has been evaluated in several studies (Innis, R. B. et al., *Eur. J. Pharmacol.*, 1987, 143, p 195–204 and Gartside, S. E., *Br. J. Phannacol.* 1995, 115, p 1064–1070, Blier, P. et al, *Trends Pharmacol. Sci.* 1994, 15, 220). In these studies it was found that $5\text{-}HT_{1A}$ receptor antagonists inhibit the decrease in firing caused by acute administration of serotonin reuptake inhibitors.

Further, treatment with a combination of pindolol (a well known $5\text{-}HT_{1A}$ receptor and β-adrenoceptor antagonist) and SSRI's has been evaluated in clinical trials. A remarkable improvement of the mood of patients was reported within one week. In addition, combined administration of pindolol and a SSRI was shown to have a good effect on patients who were non-responsive to treatment with currently available antidepressants (Artigas F. et al., *Arch. Gen. Psychiatry*, 1994, 51, p 248–251 and Blier, P. et al., *J. Clin. Psychopharmacol.* 1995, 15, p 217–222).

Several patent applications have been filed which cover the use of a combination of a $5\text{-}HT_{1A}$ antagonist and a serotonin reuptake inhibitor for the treatment of depression (see EP-A2-687 472 and EP-A2-714 663).

DE patent application No. 4414113 discloses certain 4-(indol-3-yl)-1-(indol-3-yl-alkylene)-piperidines having the general formula

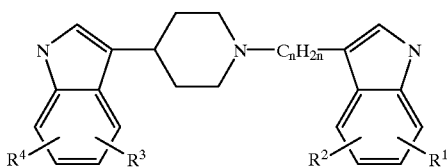

wherein n is 2–6 and the other substituents are as defined in the application. The compounds herein are claimed to have serotonin antagonistic and agonistic activities and to have effect on DOPA-accumulation in striatum and 5-HTP accumulation in N. Raphe. No biological data are given.

WO patent publication No. 94/21626 discloses compounds having the general formula

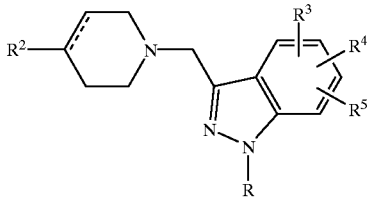

wherein $R^2$ is heteroaryl and the other substituents are as defined in the application. A compound wherein $R^2$ is 5-indolyl which is structurally closely related to the compounds of the invention is specifically mentioned herein. No data are given. The compounds are only said to give $K_i$ values of less than 1.5 μM in a test for displacement of $^3H$ spiperone from human dopamine $D_4$ receptor subtypes in clonal cell lines. WO patent publication No. 94/21627 and No. 94/21630 relate to similar compounds having affinity for human dopamine $D_4$ receptors.

WO patent publication No. 95/33721 relates to 1-(indanemethyl, dihydrobenzo-furanylmethyl, dihydrobenzothiophenylmethyl)piperidine,tetrahydropyridine, or piperazine derivatives having the general formula

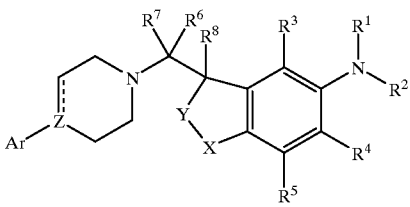

wherein one of X and Y is $CH_2$ and the other is selected from the group consisting of $CH_2$, O, or S, Ar is aryl or heteroaryl, e.g. 1-, 2-, or 3-indolyl and the other substituents is as defined in the application. The compounds interact with central 5-HT receptors, in particular with $5\text{-}HT_{1A}$ and 5-HT$_{2A}$ receptors. Some of the compounds are said to have 5-HT reuptake inhibiting effect.

OBJECT OF THE INVENTION

It is the object of the present invention to provide compounds with potent serotonin reuptake inhibiting activity as well as antagonistic properties at 5-HT$_{1A}$ receptors. Such compounds may be useful as fast onset of action medicaments for the treatment of affective disorders, such as depression.

A further object of the present invention is to provide a pharmaceutical composition comprising these compounds as active ingredients.

SUMMARY OF THE INVENTION

The invention then, inter alia, comprises the following alone or in combination:

A substituted 4-, 5-, 6-, or 7-indole or indoline derivative of formula (I)

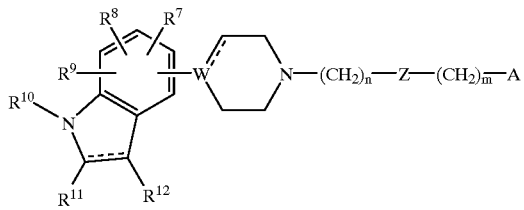

(I)

wherein W is N, C, CH or COH and the dotted lines indicate optional bonds and wherein A is a group having the formula

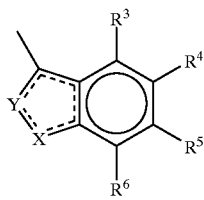

(IIA)

wherein X is CR$^{1A}$, CHR$^{1A}$, N, NR$^{1B}$, O, or S, where R$^{1A}$ is as defined for R$^3$ to R$^9$ below, and where R$^{1B}$ is as defined for R$^{10}$ below;

Y is CR$^{2A}$, CHR$^{2A}$, N, NR$^{2B}$, O, or S, where R$^{2A}$ is as defined for R$^3$ to R$^9$ below and where R$^{2B}$ is as defined for R$^{10}$ below, and the dotted lines indicate optional bonds;

provided that X and Y are not both O or S;

A is a group having the formula

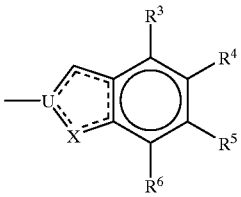

(IIB)

wherein
X is CR$^{1A}$, CHR$^{1A}$, N, NR$^{1B}$, O, or S, where R$^{1A}$ is as defined for R$^3$ to R$^9$ below, and where R$^{1B}$ is as defined for R$^{10}$ below;
U is C, CH, or N; and
the dotted lines indicate optional bonds;
A is a group having the formula

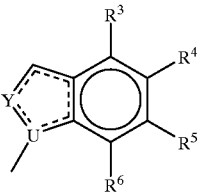

(IIC)

wherein
U is C, CH, or N;
Y is CR$^{2A}$, CHR$^{2A}$, N, NR$^{2B}$, O, or S, where R$^{2A}$ is as defined for R$^3$ to R$^9$ below and where R$^{2B}$ is as defined for R$^{10}$ below;
and the dotted lines indicate optional bonds;
n is 0, 1, 2, 3, 4, or 5, and m is 0, 1, 2, 3, 4, or 5;
Z is CH$_2$, O, S, CO, SO, or SO$_2$, provided that if n is 0 then Z is CH$_2$;
R$^3$–R$^9$ and R$^{11}$ to R$^{12}$ are independently selected from hydrogen, halogen, cyano, nitro, C$_{1-6}$-alk(en/yn)yl, C$_{1-6}$ alkoxy, C$_{1-6}$-alkylthio, hydroxy, hydroxy-C$_{1-6}$-alkyl, C$_{1-6}$-alkoxycarbonyl, C$_{3-8}$-cycloalk(en)yl, C$_{3-8}$-cycloalk(en)yl-C$_{1-6}$-alk(en/yn)yl, C$_{1-6}$-alkylcarbonyl, phenylcarbonyl, halogen substituted phenylcarbonyl, trifluoromethyl, trifluoromethylsulfonyloxy, C$_{1-6}$ alkylsulfonyl, aryl and heteroaryl, and/or two adjacent groups taken from R$^3$–R$^9$ may together form a methylenedioxy group,
and/or two adjacent groups R$^7$–R$^9$ may together form a cyclopentyl or cyclohexyl ring which may be substituted with one or more methyl groups,
and/or one of R$^3$–R$^9$ may alternatively be a group —NR$^{13}$R$^{14}$ wherein R$^{13}$ is as defined for R$^{10}$ below and R$^{14}$ is hydrogen, C$_{1-6}$-alk(en/yn)yl, C$_{3-8}$-cycloalk(en)yl, C$_{3-8}$-cycloalk(en)yl-C$_{1-6}$ alk(en/yn)yl, aryl, heteroaryl, aryl-C$_{1-6}$ alkyl, or heteroaryl-C$_{1-6}$-alkyl;
R$^{10}$ is
hydrogen, C$_{1-6}$-alk(en/yn)yl, C$_{3-8}$-cycloalk(en)yl, C$_{3-8}$-cycloalk(en)yl-C$_{1-6}$ alk(en/yn)yl, aryl, heteroaryl, aryl-C$_{1-6}$-alkyl, heteroaryl-C$_{1-6}$-alkyl, acyl, thioacyl, C$_{1-6}$-alkylsulfonyl, trifluoromethylsulfonyl, arylsulfoniyl, or heteroarylsulfonyl;
R$^{15}$VCO— wherein V is O or S and R$^{15}$ is C$_{1-6}$-alk(en/yn)yl, C$_{3-8}$-cycloalk(en)yl, C$_{3-8}$-cycloalk(en)yl-C$_{1-6}$-alk(en/yn)yl, aryl, or heteroaryl; or a group R$^{16}$R$^{17}$NCO— or R$^{16}$R$^{17}$NCS— wherein R$^{16}$ and R$^{17}$ are independently selected from hydrogen, C$_{1-6}$-alk(en/yn)yl, C$_{3-8}$-cycloalk(en)yl, C$_{3-8}$-cycloalk(en)yl-C$_{1-6}$-alk(en/yn)yl, heteroaryl, or aryl, or R$^{16}$ and R$^{17}$ together with the N-atom to which they are linked, form a pyrrolidinyl, piperidinyl, morpholinyl, or perhydroazepin group;

or an acid addition salt thereof.

In a particular embodiment, the compounds of the invention are compounds wherein A is a group of formula (IIA) including such compounds wherein A is a group having the formulas illustrated below:

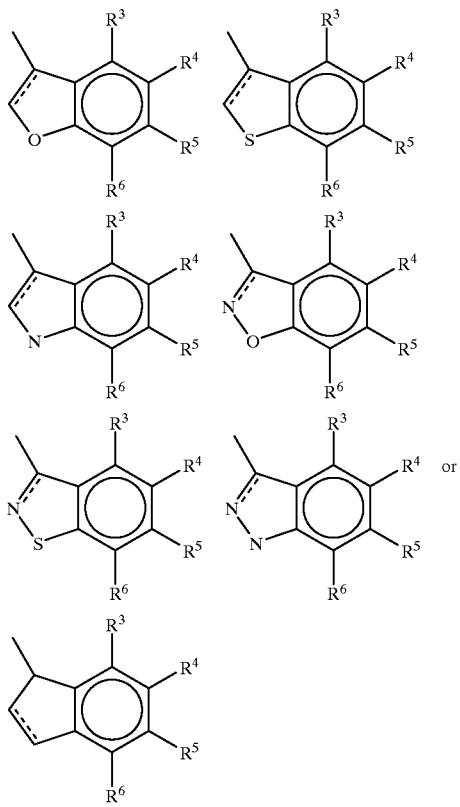

wherein R$^3$ to R$^6$ and the dotted lines are as defined above.

In a particular embodiment A is a group having the formula

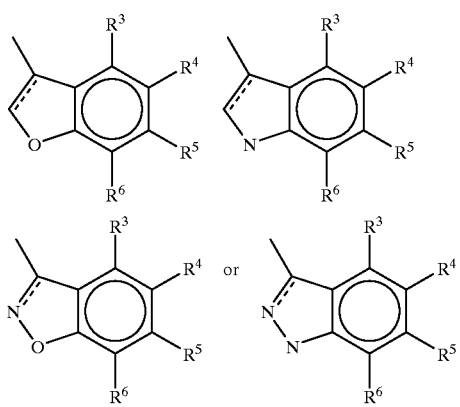

wherein R$^3$ to R$^6$ and the dotted lines are as defined above.

In another particular embodiment the present invention relates to compounds having the formula

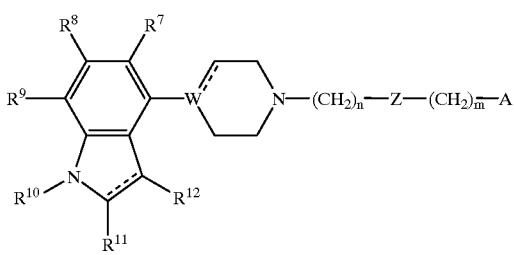

(II)

wherein R$^7$ to R$^{12}$, W, A, Z, n, m and the dotted lines are as defined above.

In a particular embodiment Z is CH$_2$ and n+m is 0, 1, 2, 3, 4, 5, or 6.

In another embodiment the present invention relates to compounds having the formula II above and A is a group having the formula IIA above.

In another particular embodiment the present invention relates to compounds having the formula II above and A is a group having the formula

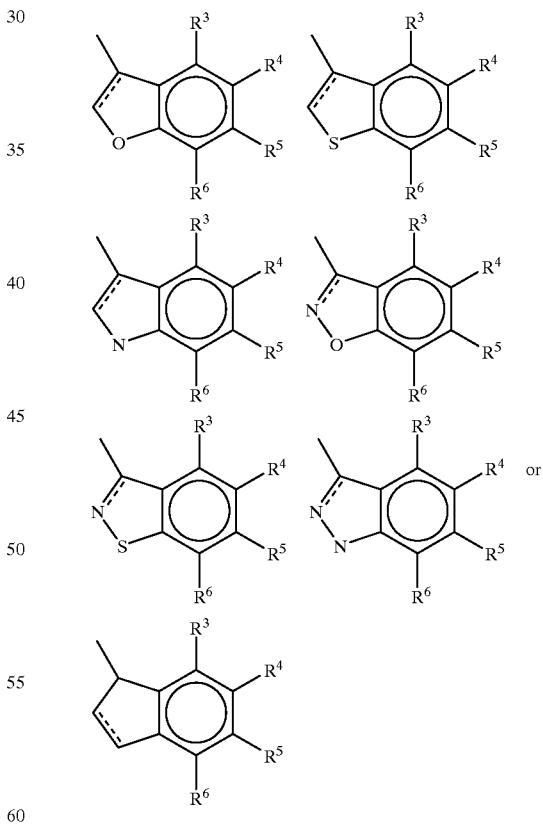

wherein R$^3$ to R$^6$ and the dotted lines are as defined above.

In a further particular embodiment the present invention relates to compounds having the formula II above and A is a group having the formula

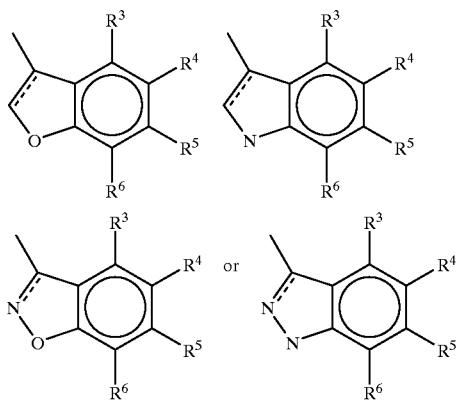

wherein R³ to R⁶ and the dotted lines are as defined above.

In a particular embodiment the compounds of the invention are the compounds wherein $R^3$–$R^9$ and $R^{11}$–$R^{12}$ is hydrogen, halogen, cyano, nitro, $C_{1-6}$-alkyl, $C_{1-6}$-alkoxy hydroxy, hydroxy-$C_{1-6}$-alkyl, $C_{1-6}$-alkoxycarbonyl and trifluoromethyl; and $R^{10}$ is hydrogen.

In another particular embodiment of the invention, W is N.

Examples of compounds according to the invention are the compounds 1-(2-(3-Benzofuranyl)ethyl)-4-(1H-indol-4-yl)piperazine,
1-(3-Benzofuranylmethyl)-4-(1H-indol-4-yl)piperazine,
1-(2-(5-Fluoro-3-benzofuranyl)ethyl)-4-(1H-indol-4-yl)piperazine,
1-(4-(5-Fluoro-3-benzofuranyl)-1-butyl)-4-(1H-indol-4-yl)piperazine,
1-(2-(1H-Indol-3-yl)ethyl)-4-(1H-indol-4-yl)piperazine,
1-(3-(1H-Indol-3-yl)-1-propyl)-4-(1H-indol-4-yl)piperazine,
1-(4-(1H-Indol-3-yl)-1-butyl)-4-(1H-indol-4-yl)piperazine,
1-(3-(5-Fluoro-3-benzofuranyl)-1-propyl)-4-(1H-indol-4-yl)piperazine,
1-(2-(2-Methyl-4,5,6,7-tetrafluoro-3-benzofuranyl)ethyl)-4-(1H-indol-4-yl)piperazine,
1-(2-(3-Indazolyl)ethyl)-4-(1H-indol-4-yl)piperazine,
1-(2-(6-Chloro-3-indazolyl)ethyl)-4-(1H-indol-4-yl)piperazine,
1-(2-(7-Cyano-1H-indol-3-yl)ethyl)-4-(1H-indol-4-yl)piperazine,
1-(2-(6-Chloro-1H-indol-3-yl)ethyl)-4-(1H-indol-4-yl)piperazine,
1-(2-(4-Chloro-1H-indol-3-yl)ethyl)-4-(1H-indol-4-yl)piperazine,
1-(2-(5-Fluoro-1H-indol-3-yl)ethyl)-4-(1H-indol-4-yl)piperazine,
1-(2-(6-Chloro-1H-indol-3-yl)ethyl)-4-(1H-indol-4-yl)-1,2,3,6-tetrahydropyridine,
1-(2-(5-Fluoro-1H-indol-3-yl)ethyl)-4-(1H-indol-4-yl)-1,2,3,6-tetrahydropyridine,
1-(2-(7-Bromo-1H-indol-3-yl)ethyl)-4-(1H-indol-4-yl)piperazine,
1-(1-Allyl-1H-indol-4-yl)-4-(2-(6-chloro-1H-indol-3-yl)ethyl)piperazine,
1-(1-Allyl-1H-indol-4-yl)-4-(2-(5-fluoro-1H-indol-3-yl)ethyl)piperazine,
1-(1-Benzyl-1H-indol-4-yl)-4-(2-(6-chloro-1H-indol-3-yl)ethyl)piperazine,
1-(1-Benzyl-1H-indol-4-yl)-4-(2-(5-fluoro-1H-indol-3-yl)ethyl)piperazine,
1-(1-Benzyl-1H-indol-4-yl)-4-(2-(5-bromo-1H-indol-3-yl)ethyl)piperazine,
1-(2-(6-Chloro-1H-indol-3-yl)ethyl)-4-(1-propargyl-1H-indol-4-yl)piperazine,
1-(2-(1H-Indol-3-yl)ethyl)-4-(1-propargyl-1H-indol-4-yl)piperazine,
1-(2-(5-Fluoro-1H-indol-3-yl)ethyl)-4-(1-propargyl-1H-indol-4-yl)piperazine,
1-(2-(5-Bromo-1H-indol-3-yl)ethyl)-4-(1-propargyl-1H-indol-4-yl)piperazine,
1-(1-Benzyl-1H-indol-4-yl)-4-(2-(1-indol-3-yl)ethyl)piperazine,
1-(2-(5-Bromo-1H-indol-3-yl)ethyl)-4-(1H-indol-5-yl)piperazine,
1-(2-(5-Chloro-1H-indol-3-yl)ethyl-(1H-indol-5-yl)piperazine,
1-(2-(5-Fluoro-1H-indol-3-yl)ethyl)-4-(6-hydroxymethyl-1H-indol-4-yl)piperazine,
1-(2-(6-Chloro-1H-indol-3-yl)ethyl)-4-(6-hydroxymethyl-1H-indol-4-yl)piperazine,
1-(2-(5-Bromo-1H-indol-3-yl)ethyl)-4-(6-hydroxymethyl-1H-indol-4-yl)piperazine,
1-(3-(6-Fluoro-1,2-benzisoxazol-3-yl)-1-propyl)-4-(1H-indol-4-yl)piperazine,
1-(2-(1H-Indol-3-yl)ethyl)-4-(6-methoxycarbonyl-1H-indol-4-yl)piperazine,
1-(2-(6-Chloro-1H-indol-3-yl)ethyl)-4-(6-methoxycarbonyl-1H-indol-4-yl)piperazine,
1-(2-(5-Fluoro-3-benzofuranyl)ethyl)-4-(6-methoxycarbonyl-1H-indol-4-yl)piperazine,
1-(5-Fluoro-3-benzofuranylmethyl)-4-(1H-indol-4-yl)piperazine,
1-(3-Cyano-1H-indol-4-yl)-4-(2-(1H-indol-3-yl)ethyl)piperazine,
1-(3-Cyano-1H-indol-4-yl)-4-(2-(5-fluoro-3-benzofuranyl)ethyl)piperazine,
1-(2-(6-Chloro-1H-indol-3-yl)ethyl)-4-(3-cyano-1H-indol-4-yl)piperazine,
1-(2-(3-Benzofuranyl)ethyl)-4-(3-cyano-1H-indol-4-yl)piperazine,
1-(1H-Indol-4-yl)-4-(2-(5-methyl-3-benzofuranyl)ethyl)piperazine,
1-(1H-Indol-4-yl)-4-(2-(4-methyl-3-benzofuranyl)ethyl)piperazine,
1-(3-(5-Fluoro-3-benzofuranyl)-1-propyl)-4-(1H-indol-4-yl)-1,2,3,6-tetrahydropyridine,
1-(2-(5-Chloro-3-benzofuranyl)ethyl)-4-(1H-indol-4-yl)piperazine,
1-(1H-Indol-4-yl)-4-(2-(6-methyl-3-benzofuranyl)ethyl)piperazine,
1-(2-(7-Chloro-3-benzofuranyl)ethyl)-4-(1H-indol-4-yl)piperazine,
1-(2-(4-Chloro-1H-indol-3-yl)ethyl)-4-(3-cyano-1H-indol-4-yl)piperazine,
1-(2-(6-Chloro-1H-indol-3-yl)ethyl-4-(1H-indol-4-yl)piperidine,
1-(2-(5-Chloro-1H-indol-3-yl)ethyl)-4-(1H-indol-4-yl)piperazine, 1-(2-(7-Bromo-1H-indol-3-yl)ethyl)-4-(1H-indol-4-yl) piperazine, 1-(2-(4-Chloro-1H-indol-3-yl)ethyl)-4-(1H-indol-4-yl) piperazine, 1-(2-(6-Trifluoromethyl-1H-indol-3-yl)ethyl)-4-(1H-indol-4-yl)piperazine, 1-(1H-Indol-4-yl)-4-(2-(5-methyl-1H-indol-3-yl)ethyl) piperazine, 1-(1H-Indol-4-yl)-4-(2-(6-methyl-1H-indol-3-yl)ethyl) piperazine, 1-(1H-Indol-4-yl)-4-(2-(7-methyl-1H-indol-3-yl)ethyl) piperazine, 1-(2-(4,5-Dichloro-3-benzofuranyl)ethyl)-4-(1H-indol-4-yl)piperazine, 1-(2-(5-Bromo-3-benzofuranyl)ethyl)-4-(1H-indol-4-yl) piperazine, 1-(2-(4-Chloro-1H-indol-3-yl)ethyl)-4-(1H-indol-4-yl) piperidine, 4-(1H-Indol-4-yl)-1-(2-(5-methyl-1H-indol-3-yl)ethyl) piperidine, 4-(1H-Indol-4-yl)-1-(2-(1H-indol-3-yl)ethyl)piperidine, 1-(1H-Indol-4-yl)-4-(3-(4-methyl-3-benzofuranyl)-1-propyl)piperazine, 4-(1H-Indol-4-yl)-1-(3-(4-methyl-3-benzofuranyl)-1-propyl)piperidine, 1-(3-(4-Chloro-3-benzofuranyl)-1-propyl)-4-(1H-indol-4-yl)piperazine, 1-(2-(6-Chloro-1H-indol-3-yl)ethyl)-4-(6-chloro-1H-indol-4-yl)piperazine, 1-(2-(6-Chloro-1H-indol-3-yl)ethyl)-4-(6-fluoro-1H-indol-4-yl)piperazine, 1-(2-(6-Chloro-1H-indol-3-yl)ethyl)-4-(6-cyano-1H-indol-4-yl)piperazine, 1-(2-(6-Chloro-1H-indol-3-yl)ethyl)-4-(7-chloro-1H-indol-4-yl)piperazine, 1-(2-(6-Chloro-1H-indol-3-yl)ethyl)-4-(7-cyano-1H-indol-4-yl)piperazine, 1-(2-(6-Chloro-1H-indol-3-yl)ethyl)-4-(2-cyano-1H-indol-4-yl)piperazine, 1-(2-(6-Chloro-1H-indol-3-yl)ethyl)-4-(1H-indolin-4-yl) piperazine, 1-(2-(6-Chloro-1H-indol-3-yl)ethyl)-4-(1H-indol-6-yl) piperazine and 1-(2-(6-Chloro-1H-indol-3-yl)ethyl)-4-(1H-indol-7-yl) piperazine, or an acid addition salt thereof.

The invention also relates to a pharmaceutical composition comprising a compound of the invention or a pharmaceutically acceptable acid addition salt thereof and at least one pharmaceutically acceptable carrier or diluent.

In another aspect the invention relates to the use of a compound of the invention or a pharmaceutically acceptable acid addition salt thereof for the preparation of a medicament for the treatment of a disorder or disease responsive to the inhibition of serotonin reuptake and antagonism of 5-HT$_{1A}$ receptors.

In a final object, the present invention relates to a method for the treatment of a disorder or disease of living animal body, including a human, which is responsive to the inhibition of serotonin reuptake and antagonism of 5-HT$_{1A}$ receptors comprising administering to such a living animal body, including a human, a therapeutically effective amount of a compound as above or a pharmaceutically acceptable acid addition salt thereof.

Diseases or disorders responsive to the inhibition of serotonin re-uptake and antagonistic activity at 5-HT$_{1A}$ receptors include affective disorders, such as depression, psychosis, anxiety disorders including general anxiety disorder and panic disorder and obsessive compulsive disorder.

Due to their combined antagonism of 5-HT$_{1A}$ receptors and serotonin reuptake inhibiting effect, the compounds of the invention are particularly useful as fast onset of action medicaments for the treatment of depression. The compounds may also be useful for the treatment of depression in patients who are resistant to treatment with currently available antidepressants.

In the groups of formula (IIA), (IIB) and (IIC), the presence and position of double bonds in the ring containing X, U and Y depend on the meaning of X, U and Y.

Thus, as regards the group of formula (IIA), it is very clear to a person skilled in the art, that when a dotted line emanating from X is a bond, then X is N or CR$^{1A}$, and when the dotted line is not a bond then X is CHR$^{1A}$, NR$^{1B}$, O, or S; and when a dotted line emanating from Y is a bond, then Y is N, or CR$^{1B}$ and when the dotted line is not a bond Y is CHR$^{2A}$, NR$^{2B}$, O, or S.

Further, as regards the group of formula (IIB), it is very clear to a person skilled in the art, that when a dotted line emanating from X is a bond then X is N, or CR$^{1A}$ and when the dotted line is not a bond then X is CH$^{1A}$, NR$^{1B}$, O, or S; and when a dotted line emanating from U is a bond then U is C and when the dotted line is not a bond U is CH, or N.

And finally as regards the group of formula (IIC), it is very clear to a person skilled in the art that when a dotted line emanating from U is a bond then U is C and when the dotted line is not a bond U is CH, or N; and when a dotted line emanating from Y is a bond then Y is N, or CR$^{2A}$ and when the dotted line is not a bond then Y is CHR$^{2A}$, NR$^{2B}$, O, or S.

The same applies to W, which is N, CH, or COH when the dotted line emanating from W does not indicate a bond and C when it indicates a bond.

The expression C$_{1-6}$-alk(en/yn)yl means a C$_{1-6}$-alkyl, C$_{2-6}$-alkenyl, or a C$_{2-6}$-alkynyl group. The expression C$_{3-8}$-cycloalk(en)yl means a C$_{3-8}$-cycloalkyl- or cycloalkenyl group.

The term C$_{1-6}$ alkyl refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl.

Similarly, C$_{2-6}$ alkenyl and C$_{2-6}$ alkynyl, respectively, designate such groups having from two to six carbon atoms, including one double bond and one triple bond respectively, including but not limited to ethenyl, propenyl, butenyl, ethynyl, propynyl, and butynyl.

The terms C$_{1-6}$ alkoxy, C$_{1-6}$ alkylthio, C$_{1-6}$ alkylsulfonyl, C$_{1-6}$ alkylamino, C$_{1-6}$ alkylcarbonyl, hydroxy-C$_{1-6}$-alkyl etc. designate such groups in which the C$_{1-6}$ alkyl is as defined above.

The term C$_{3-8}$ cycloalkyl designates a monocyclic or bicyclic carbocycle having three to eight C-atoms, including but not limited to cyclopropyl, cyclopentyl, cyclohexyl, etc.

The term C$_{3-8}$ cycloalkenyl designates a monocyclic or bicyclic carbocycle having three to eight C-atoms and including one double bond.

In the term C$_{3-8}$-cycloalk(en)yl-C$_{1-6}$-alk(en/yn)yl, C$_{3-8}$-cycloalk(en)yl and C$_{1-6}$-alk(en/yn)yl are as defined above.

The term aryl refers to a carbocyclic aromatic group, such as phenyl, naphthyl, in particular phenyl. As used herein aryl may be substituted one or more times with halogen, nitro, cyano, trifluoromethyl, C$_{1-6}$-alkyl, hydroxy and C$_{1-6}$-alkoxy.

The term heteroaryl refers to a mono- or bicyclic heterocyclic group such as indolyl, thienyl, pyrimidyl, oxazolyl, isoxazolyl, thiazolyl, isothiazolyl, imidazolyl, benzofuiranyl, benzothienyl, pyridyl and furanyl, in particular pyrimidyl, indolyl, and thienyl.

As used herein heteroaryl may be substituted one or more times with halogen, nitro, cyano, trifluoromethyl, $C_{1-6}$-alkyl, hydroxy and $C_{1-6}$-alkoxy.

In aryl-$C_{1-6}$-alkyl and heteroaryl-$C_{1-6}$-alkyl, aryl, heteroaryl and $C_{1-6}$-alkyl is as defined above.

Halogen means fluoro, chloro, bromo or iodo.

As used herein the term acyl refers to formyl, $C_{1-6}$-alk(en/yn)ylcarbonyl, arylcarbonyl, aryl-$C_{1-6}$-alk(en/yn)ylcarbonyl, $C_{3-8}$-cycloalk(en)ylcarbonyl, or a $C_{3-8}$-cycloalk(en)yl-$C_{1-6}$alk(en/yn)yl-carbonyl group and the term thioacyl is as the corresponding acyl group in which the carbonyl group is replaced with a thiocarbonyl group.

The acid addition salts of the invention are preferably pharmaceutically acceptable salts of the compounds of the invention formed with non-toxic acids. Exemplary of such organic salts are those with maleic, fiunaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric, and nitric acids.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention contain chiral centres and such compounds exist in the form of isomers (i.e. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g., by fractional crystallization of d- or 1-(tartrates, mandelates, or camphorsulphonate) salts for example. The compounds of the present invention may also be resolved by the formation of diastereomeric derivatives.

Additional methods for the resolution of optical isomers, known to those skilled in the art, may be used. Such methods include those discussed by J. Jaques, A. Collet, and S. Wilen in "Enantiomers, Racemates, and Resolutions", John Wiley and Sons, New York (1981).

Optically active compounds can also be prepared from optically active starting materials.

Finally, formula (I) includes any tautomeric forms of the compounds of the invention.

The compounds of the invention can be prepared by one of the following methods comprising:

a) reducing the carbonyl groups of a compound of formula (III)

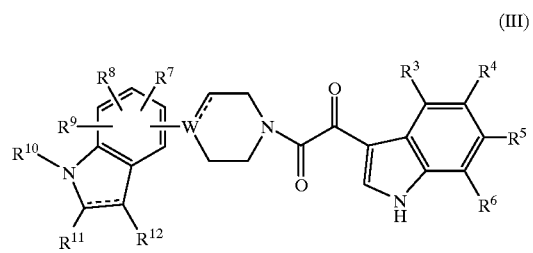
(III)

wherein $R^3$–$R^{12}$, W and the dotted lines are as defined above;

b) alkylating an amine of formula (IV)

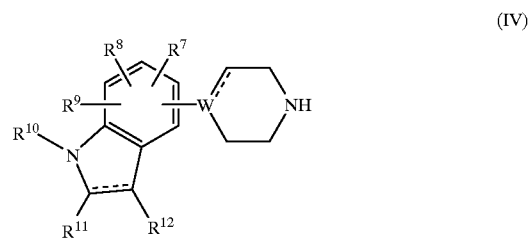
(IV)

wherein $R^7$–$R^{12}$, W and the dotted lines are as defined above with a reagent of formula (V)

G—(CH$_2$)$_n$—Z—(CH$_2$)$_m$—A      (V)

wherein A, Z, n, and m are as defined above and G is a suitable leaving group such as halogen, mesylate, or tosylate;

c) reductive alkylation of an amine of formula

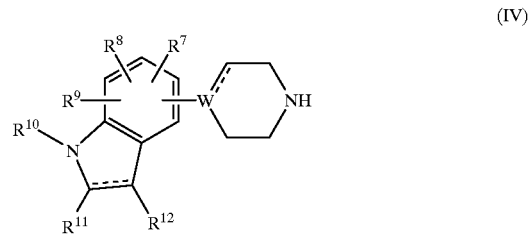
(IV)

wherein $R^7$–$R^{12}$, W and the dotted lines are as defined above with a reagent of formula (VI)

E—(CH$_2$)$_n$—Z—(CH$_2$)$_m$—A      (VI)

wherein A, Z, n and m are as defined above and E is either an aldehyde or a carboxylic acid group;

d) reducing the double bond of the indole ring, which is attached to the cyclic amine moiety, of formula (I) in order to obtain the corresponding 2,3-dihydroindole derivatives;

e) reducing the double bond of a tetrahydropyridine of formula (VII)

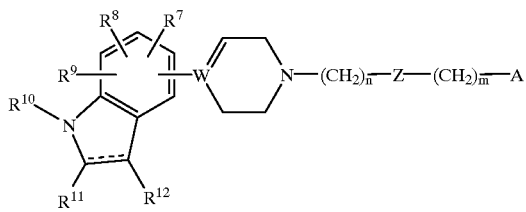

(VII)

wherein $R^{17}$–$R^{12}$, A, Z, n, m, and the dotted lines are as previously defined, on order to obtain the corresponding piperidine derivatives;

f) reducing the amide group of a compound of formula (VIII)

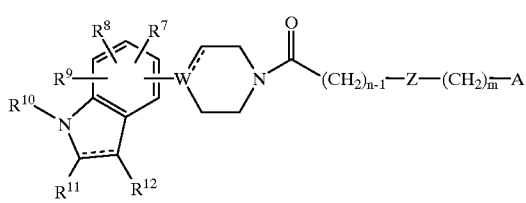

(VIII)

wherein $R^7$–$R^{12}$, A, W, Z, n, m, and the dotted lines are as previously defined;

g) reductive removal of one or more of the halogen substitutents $R^3$–$R^9$ and $R^{11}$–$R^{12}$ in a compound of formula (I) in which one or more of these substituents are selected from chloro, bromo, or iodo;

h) dialkylating an amine of formula (IX)

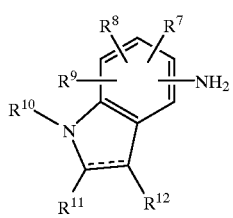

(IX)

wherein $R^7$–$R^{12}$ and the dotted line are as defined above with a reagent of formula (X)

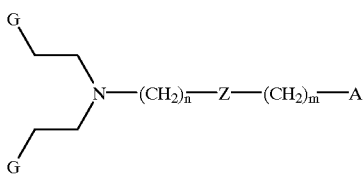

(X)

wherein A, Z, n, and m are as defined above and G is a suitable leaving group such as halogen, mesylate, or tosylate;

i) dialkylating an amine of formula (XI)

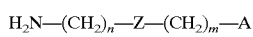

$H_2N$—$(CH_2)_n$—Z—$(CH_2)_m$—A (XI)

wherein A, Z, n, and m are as defined above with a reagent of formula (XII)

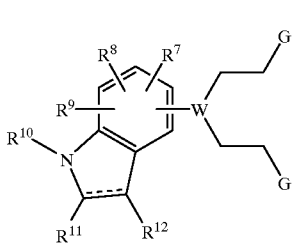

(XII)

wherein $R^7$–$R^{12}$, W, and the dotted line are as defined above and G is a suitable leaving group such as halogen, mesylate, or tosylate;

j) alkylating, arylating, or acylating one or both indole nitrogen atoms of a compound of formula (I) in which $R^{10}$ is hydrogen, and/or X and/or Y is NH; or k) reducing a compound of formula (I) in which $R^7$, $R^8$, or $R^9$ is an alkoxycarbonyl group in order to obtain the corresponding hydroxymethyl group;

whereupon the compounds of formula (I) are isolated as the free base or in the form of an acid addition salt thereof.

The reduction according to method a) is preferably carried out in an inert organic solvent such as diethyl ether or tetrahydrofuran in the presence of lithium aluminium hydride at reflux temperature. Starting compounds of formula (TII) are generally prepared by condensation of 3-chlorooxalyl indoles (prepared as described in Houben-Weyl, Methoden der Organischen Chemie, Vol E6B2, p. 1058) with amines of formula (IV) in the presence of a base such as triethylamine or potassium carbonate.

The alkylation according to method b) is conveniently performed in a inert organic solvent such as a suitably boiling alcohol or ketone, preferably in the presence of an organic or inorganic base (potassium carbonate or triethylamine) at reflux temperature.

Indolylpiperazine derivatives of formula (IV) are conveniently prepared from the corresponding arylamine according to the method described by Martin et al, J. Med. Chem. 32 (1989) 1052, or the method described by Kruse et al, Rec. Trav. Chim. Pays-Bas 107 (1988) 303. The starting arylamines are either commercially available or are well-described in the literature.

Indolyl tetrahydropyridine derivatives of formula (IV) are known from literature (see eg. French Pat. 2458549). Conveniently, 1-protected 4, 5, 6, or 7-bromoindole is lithiated with BuLi followed by addition of 1-protected 4-piperidone and subsequent dehydration as outlined in an example below. The starting bromoindoles are either commercially available or well-described in the literature. Reagents of formula (V) are either commercially available or can be prepared by literature methods, eg. from the corresponding carboxylic acid derivative by reduction to the corresponding hydroxy derivatives and subsequent conversion of the hydroxy group to the group G by conventional methods.

The reductive alkylation according to method c) is performed by standard literature methods. The reaction can be performed in two steps, ie. coupling of derivatives of formula (IV) and the reagent of formula (VI) by standard methods via the carboxylic acid chloride or by use of coupling reagents such as eg. dicyclohexyl carbodiimide followed by reduction of the resulting amide with lithium aluminium hydride or alane. The reaction can also be performed by a standard one-pot procedure. Carboxylic acids or aldehydes of formula (VI) are either commercially available or described in the literature.

Reduction of the indole double bond according to method d) is conveniently performed by treatment with diborane or a diborane precursor such as the trimethylamine or dimethylsulfide complex in an inert solvent such as eg. tetrahydrofaran or dioxane from 0° C. to reflux temperature followed by acid catalyzed hydrolysis of the intermediate borane derivative. The reduction can alternatively be performed by treatment with sodium cyanoborohydride in trifluoroacetic acid.

Reduction of the double bonds according to method e) is most conveniently performed by hydrogenation in an alcohol in the presence of a noble metal catalyst, such as eg. platinum or palladium.

Reduction of amide groups according to method f) is most conveniently performed with lithium aluminium hydride or alane in an inert organic solvent such as eg. tetrahydrofaran or diethylether from 0° C. to reflux temperature.

The removal of halogen substituents according to method g) is conveniently performed by catalytic hydrogenation in an alcohol in the presence of a palladium catalyst or by treatment with ammomium formate in an alcohol at elevated temperatures in the presence of a palladium catalyst.

The dialkylation of amines according to methods h) and i) is most conveniently performed at elevated temperatures in an inert solvent such as eg. chlorobenzene, toluene, N-methylpyirolidinone, dimethylformamide, or acetonitrile. The reaction might be performed in the presence of base such as eg. potassium carbonate or triethylamine. Starting material for processes h) and i) are commercially available or can be prepared using conventional methods.

The indole N-alkylation or N-acylation are performed in an inert solvent such as eg. an alcohol or ketone at elevated temperatures in the presence of base, eg. potassium carbonate or triethylamine. Alternatively, a phase-transfer reagent can be used. The corresponding N-arylation is best performed under Ullmann-conditions as described in the literature.

The reduction of alkoxycarbonyl groups according to method k) is most conveniently performed with lithium aluminium hydride or alane in an inert organic solvent such as e.g. tetrahydrofuran.

The following examples will illustrate the invention further. They are, however, not to be construed as limiting.

EXAMPLES

Melting points were determined on a Büichi B-540 apparatus and are uncorrected. Mass spectra were obtained on a Quattro MS—MS system from VG Biotech, Fisons Instruments or on a Sciex API 150EX from Perkin Elmer. Spectra were obtained at two sets of operating conditions using electrospray ionisation: one set to obtain molecular weight information (MH+, 20 eV) and the other set to induce fragmentation patterns (70–100 eV). The background was substracted. The relative intensities of the ions are obtained from the fragmentation pattern. When no intensity is indicated for the molecular ion (MH+) this ion was only present under the first set of operating conditions. $^1$H NMR spectra were recorded at 250 MHz on a Bruker AC 250 or at 500 MHz on a Bruker DRX 500. Deuterated chloroform (99.8% D) or dimethylsulfoxide (99.9% D) were used as solvents. TMS was used as internal reference standard. Chemical shifts are expressed as ppm values. The following abbreviations are used for multiplicity of NMR signals: s=singlet, d=doublet, t=triplet, quartet, qv=quintet, h=heptet, dd=double doublet, dt=double triplet, dq=double quartet, tt=riplet of triplets, m=multiplet, b=broad. NMR signals corresponding to acidic protons are to some extent omitted. Content of water in crystalline compounds were determined by Karl Fischer titration. Proper elemental analysis for all target compounds were obtained. Standard work-up procedures refer to extraction with the indicated organic solvent from proper aqueous solutions, drying of combined organic extracts (anhydrous $MgSO_4$ or $NaSO_4$), filtering, and evaporation of the solvent in vacuo. For column chromatography silica gel of type Kieselgel 60, 40–60 mesh ASTM was used.

PREPARATION OF INTERMEDIATES

A. Preparation of 1-(1H-indol-4-yl)piperazines
1-(1H-indol-4-yl)piperazine

Dinitrotoluene (25 g) was dissolved in DMSO (60 mL). Triton-B (40% in methanol, 6.4 mL) was added resulting in a dark purple solution. The mixture was heated to 30° C. followed by slow addition of a solution of paraformaldehyde (4.5 g) in DMSO (40 mL). After addition the mixture was heated to 65° C. for 1.5 hours. Standard work-up with ethyl acetate gave 2-(2,6-dinitrophenyl)ethanol (29 g) as a dark red oil. The oil (27 g) was dissolved in ethanol (250 mL) and 5% palladium on charcoal (3 g) was added. The mixture was treated with hydrogen gas at 3 atmospheres of pressure in a Parr apparatus for 16 h. Filtration and removal of solvent in vacuo gave 2-(2,6-diaminophenyl)ethanol (19.4 g) as brown oil that crystallized upon standing. Part of this product (15.8 g) was dissolved in toluen (250 mL) and tris (triphenylphosphine)ruthenium(II)chloride (2.9 g) was added. The mixture was refluxed with a water separator for 8 hours followed by removal of solvent in vacuo.

The remaining reaction mixture was purified by flash chromatography (eluent: heptane/ethyl acetate 3:1) giving 4-amino-1H-indole as a crystalline solid (7.6 g). The solid was dissolved in chlorobenzene (150 mL) and bis(2-chloroethyl)amine hydrochloride (9 g) was added followed by reflux for 90 hours. Filtration gave a crystalline product (9.2 g) which was heated in a mixture of conc. aq. ammonia (50 mL) and ethyl acetate (200 mL) for 15 min. Separation of the organic phase, drying and evaporation gave the titel compound as a crystalline material (5.6 g).

The following piperazines were prepared analogously:
1-(6-Methoxycarbonyl-1H-indol-4-yl)piperazine.
1-(6-t-Butyl-5-methoxy-1H-indol-4-yl)piperazine.
1-(6-t-Butyl-7-methoxy-1H-indol-4-yl)piperazine.
1-(6,7-Dihydro-6,6,8,8-tetramethylcyclopent(g)-1H-indol-4-yl)piperazine
1-(1H-indol-5-yl)piperazine This piperazine was prepared by treatment of 5-aminoindole with and bis(2-chloroethyl)amine by a procedure analogous to the procedure described above for the preparation of 1-(1H-indol-4-yl)piperazine.
1-(3-Cyano-1H-indol-4-yl)piperazine.

A mixture of 1-(1H-indol-4-yl)piperazine hydrochloride (1 g) and potassium carbonate (2.9 g) in tetrahydrofaran (25 mL) and water (25 mL) was stirred for 15 min followed by addition of a solution of di-t-butyl dicarbonate (2.3 g) in a 1:1 mixture of tetrahydrofuran and water (20 mL). The mixture was stirred at 50° C. for 16 hours. Standard work-up with ethyl acetate gave 1-t-butoxycarbonyl-4-(1H-indol-4-yl)piperazine as a heavy oil (1.1 g).

The oil was dissolved in acetonitrile (50 mL) followed by dropwise addition of chlorosulfonyl isocyanate (1 mL) at −20° C. The mixture was kept at low temperature during dropwise addition of dimethylformamide (5 mL) over 20 min. Finally, the mixture was stirred for 30 min at 0° C. An aqueous solution of sodium carbonate (30 mL) was added and the mixture stirred for 30 min. The organic phase was separated, dried and concentrated. The resulting oil was purified by column chromatography (eluent: ethyl acetate/heptane/methanol 16:3:1) giving 1-t-butoxycarbonyl-4-(3-cyano-1H-indol-4-yl)piperazine as a yellow oil (0.5 g).

The oil was dissolved in methanol (2 mL) and etheral hydrogenchloride (20 mL) was added. Stirring for 2 hours and filtration gave the title compound as a crystalline material (0.34 g).

1-(1-Allyl-1H-indol-4-yl)piperazine.

A solution of 1-t-butoxycarbonyl-4-(1H-indol-4-yl)piperazine (prepared as described above) in tetrahydrofuran (50 mL) was added dropwise to a suspension of sodium hydride (0.7 g of a 60% mineral oil suspension) in tetrahydrofuran (150 mL) at room temperature. After stirring for further 30 min a solution of allyl bromide (3.5 mL) in tetrahydrofuran (50 mL) was added dropwise. After stirring for 48 h the mixture was poured onto ice-water followed by standard work-up with ethyl acetate giving an oil, which was purified by flash chromatography (eluent: heptane/ethyl acetate 85:15) giving 1-t-butoxycarbonyl-4-(1-allyl-1H-indol-4-yl)piperazine as an oil (3.2 g). The oil was dissolved in methanol (15 mL) and a saturated solution of HCl in diethyl ether (100 mL) was added. After stirring for 16 h at room temperature, the resulting colorless crystals consisting of the hydrochloride of the title compound (2.5 g) was collected by filtration and dried in vacuo.

The following piperazines were prepared analogously:

1-(1-Benzyl-1H-indol-4-yl)piperazine 1-(1-Propargyl-1H-indol-4-yl)piperazine

B. Preparation of 4-(1H-indol-4-yl)-1,2,3,6-tetrahydropyridine

A solution of 4-bromo-1H-indole (36 g) in dimethylformamide (80 mL) was treated with a suspension of NaH (60% in mineraloil, 6.9 g) in dimethylformamide (200 mL) at 20° C. After stirring for 30 min the mixture was cooled to −10° C. an treated portionwise with t-butyldimethylsilyl chloride (38 g) followed by stirring for 1 h at room temperature. Standard work-up with ethyl acetate gave and oil which was purified by flash chromatography giving 4-bromo-1-(t-butyldimethylsilyl)-1H-indole (38 g) as a crystalline material.

The product was dissolved in dry tetrahydrofuran (500 mL), cooled to −78° C., and treated dropwise with 1.6 M BuLi in hexane (154 mL). After stirring for 30 min at −78° C., a solution of 1-carbethoxy4-piperidone (18.2 mL) in tetrahydrofaran (200 mL) was added dropwise followed by stirring for 16 h under slow raise in temperature to room temperature. Standard work-up with diethyl ether gave and oil which was purified by flash chromatography (eluent: heptane/ethyl acetate/triethylamine 6:3:1) giving 1-(t-butyldimethylsilyl)-4-(1-carbethoxy-4-hydroxy-4-piperidinyl)-1H-indole as a crystalline compound (20.5 g).

Treatment of this product with trifluoroacetic acid (15 mL) in methylene chloride (250 mL) at 0° C. for 20–30 min (reaction is followed by thin layer chromatography on silica gel, eluent ethyl acetate/heptane/triethylamine 10:9:1). Addition of 2 M sodium hydroxide, separation of the organic phase, drying, and removal of solvent in vacuo gave an oil, which was purified by flash chromatograph (eluent as mentioned above for TLC) giving 1-carbethoxy-4-(1H-indol-4-yl)-1,2,3,6-tetrahydropyridine (9.1 g) as a crystalline material.

Treatment with potassium hydroxide (5 g) in ethanol (150 mL) with a small amount of water (2 mL) at reflux for 3 days gave after standard work-up the titel compound as a yellow oil (4.5 g).

C. Preparation of 5-fluorobenzofuran-3-yl acetic acid.

A solution of 5-fluorobenzofuran-3-carboxylic acid (56 g) and saturated etheral solution of hydrochloric gas (300 mL) in methanol (600 mL) was stirred for 16 h at room temperature. Further etheral HCl was added (300 mL) followed by stirring for 24 h. Concentration in vacuo gave a dark crystalline material, methyl 5-fluorobenzofuran-3-carboxylate (58 g).

Lithium aluminium hydride (15 g) was suspended in tetrahydrofuran (400 mL) under a nitrogen atmosphere followed by dropwise addition of a solution of methyl 5-fluorobenzofuran-3-carboxylate (58 g) in tetrahydrofuran (300 mL). The temperature increased to 55° C. during the addition. After stirring for 2 h the reaction was quenched succesively with water (30 mL), 15% aq. sodium hydroxide (15 mL), and water (75 mL). Further tetrahydrofuran (500 mL) was added and the mixture stirred for 1 h. The mixture was filtered and the precipitate extracted with a mixture of methylene chloride (1 L) and ethanol (0.5 L). The combined organic phases were concentrated in vacuo giving an oil which was applied to silica gel flash chromatography (eluent: methylene chloride/25% aq. $NH_3$ 99:1). The resulting yellow oil, 5-fluorobenzofuran-3-ylmethanol (14.4 g) crystallised on standing. A solution of 5-fluorobenzofuran-3-ylmethanol (14 g) in methylene chloride (250 mL) was treated succesively with 5 drops of dimethylformamide and thionyl chloride (28 mL). After stirring for 16 h at room temperature the reaction was concentrated in vacuo giving 3-chloromethyl-5-fluorobenzofuran as an oil (19.4 g). A suspension of sodium cyanide (10 g) in dimethylsulfoxide (150 mL) was heated to 80° C. followed by quick addition of a solution of 3-chloromethyl-5-fluorobenzofuran (10 g) in dimethylsulfoxide (50 mL). The mixture was kept at 80° C. for ½ h and then poured onto ice. Standard work-up with diethyl ether gave a dark crystalline material, 5-fluorobenzofuran-3-ylacetonitrile (8.8 g).

A solution of 5-fluorobenzofuran-3-ylacetonitrile (8.8 g) in methanol (350 mL) was treated with a saturated etheral solution of hydrochloric gas (350 mL) and stirred for 16 h at room temperature. The mixture was concentrated in vacuo and standard work-up with diethyl ether/water gave methyl 5-fluorobenzofuran-3-ylacetate (9.4 g) as an oil.

The obtained methyl ester was dissolved in methanol (200 mL) and 6 M aq. sodium hydroxide (400 mL) was added followed by stirring for 16 at room temperature. Organic solvent was removed in vacuo followed by acidification with 6 M hydrochloric acid. Standard work-up with ethyl acetate gave 5-fluorobenzofuran-3-ylacetic acid (9.2 g) as a crystalline material.

The following benzofuran-3-acetic acids were prepared analogously:

2-Methyl-4,5,6,7-tetrafluorobenzofuran-3-acetic acid

Benzofuran-3-acetic acid

6-Methylbenzofuran-3-acetic acid

5-Methylbenzofuran-3-acetic acid

4-Methylbenzofuran-3-acetic acid

7-Chlorobenzofuran-3-acetic acid

5-Chlorobenzofuran-3-acetic acid

5-Fluorobenzofuran-3-propionic acid and -butanoic acid, respectively, were prepared by chain prolongation procedures analogously to the procedure described above.

6-Chloroindazol-3-acetic acid was prepared according to J. Med. Chem. 35 (1992) 2155.

3-(6-Fluorobenz[1,2]isoxazol-3-yl)propionic acid was prepared according to Drug Design Discov. 8 (1992) 225.

Preparation of the Compounds of the Invention

Example 1

1a. 1-(2-(3-Benzofuranyl)ethyl)-4-(1H-indol-4-yl)piperazine, oxalate.

A mixture of 2-(3-benzofuranyl)acetic acid (0.95 g), 1-(1H-indol-4-yl)piperazine (1.3 g), and N,N-dicyclohexylcarbodiimide (1.3 g) in a mixture of dry tetrahydrofuran (50 mL) and dry dimethylformamide (10 mL) was stirred for 16 h at room temperature. Filtration and removal of solvent in vacuo gave an oil which was purified by flash chromatography (eluent: ethyl acetate/heptane/triethylamine 10:9:1) giving 1-(3-benzofuranyl)methylcarbonyl-4-(1H-indol-4-yl)piperazine (0.5 g) as an oil. The oil was dissolved in tetrahydrofuran (20 mL) and treated with a suspension of lithium aluminium hydride (0.26 g) in tetrahydrofuran (20 mL) at room temperature under a nitrogen atmosphere followed by reflux for 4 hours. The reaction mixture was cooled to 0° C. and treated subsequently with water (1 mL), 15% aq. sodium hydroxide (0.5 mL), and water (2.5 mL). After stirring for 30 min the mixture was filtered and concentrated. The remaining oil was dissolved in acetone followed by addition of oxalic acid and filtration, giving the title compound as a crystalline material (0.4 g). Mp 130–32° C. $^1$H NMR (DMSO-$d_6$): 3.05–3.15 (m, 2H); 3.15–3.30 (m, 6H); 3.35 (s, 4H); 6.45 (s, 1H); 6.55 (d, 1H); 7.00 (t, 1H); 7.10 (d, 1H); 7.20–7.40 (m, 3H); 7.60 (d, 1H); 7.75 (d, 1H); 7.90 (s, 1H); 11.10 (s, 1H). MS m/z (%): 346 (MH+, 3%), 214 (31%), 199 (19%), 171 (14%).

The following compounds were prepared analogously:

1b, 1-(3-Benzofuranylmethyl)-4-(1H-indol-4-yl)piperazine, oxalate.

Mp 226–28° C. $^1$H NMR (DMSO-$d_6$): 3.10–3.20 (m, 4H); 3.20–3.40 (m, 4H); 4.25 (s, 2H); 6.40 (t, 1H); 6.45 (d, 1H); 7.00 (t, 1H); 7.10 (d, 1H); 7.25 (dt, 1H); 7.30–7.45 (m, 2H); 7.65 (dd, 1H); 7.95 (dd, 1H); 8.15 (s, 1H); 11.10 (s, 1H). MS m/z (%): 332 (MH+, 10%), 158 (10%), 131 (100%).

1c, 1-(2-(5-Fluoro-3-benzofuranyl)ethyl)-4-(1H-indol-4-yl)piperazine, oxalate.

Mp 196–97° C., $^1$H NMR (DMSO-$d_6$): 3.05 (t, 2H); 3.20–3.45 (m, 10H); 6.44 (s, 1H); 6.50 (d, 1H); 7.00 (t, 1H); 7.10 (d, 1H); 7.20 (dt, 1H); 7.30 (t, 1H); 7.55–7.65 (m, 2H); 8.00 (s, 1H); 11.12 (s, 1H), MS m/z (%): 364 (MH+, 7%), 214 (42%), 199 (20%), 171 (14%).

1d, 1-(4-(5-Fluoro-3-benzofuranyl)-1-butyl)-4-(1H-indol-4-yl)piperazine, dihydrochloride.

Mp 241–44° C., $^1$H NMR (DMSO-$d_6$): 1.65–1.95 (mn 4H); 2.70 (t, 2H); 3.15–3.40 (m, 6H); 3.60 (d, 2H); 3.70 (d, 2H); 6.50 (s, 1H); 6.55 (d, 1H); 7.00 (t, 1H); 7.10 (d, 1H); 7.15 (dt, 1H); 7.30 (t, 1H); 7.45–7.60 (m, 2H); 7.90 (s, 1H); 10.95 (b, 1H); 11.20 (s, 1H). MS m/z (%): 392 (MH+, 90%), 234 (19%), 199 (23%), 163 (49%), 131 (11%)

1e, 1-(2-(1H-indol-3-yl)ethyl)-4-(1H-indol-4-yl)piperazine, hemioxalate.

Mp 167–69° C., $^1$H NMR (DMSO-$d_6$): 3.05 (s, 4H); 3.15 (s, 4H); 3.30 (s, 4H); 6.40 (s, 1H); 6.50 (d, 1H); 6.90–7.15 (m, 4H); 7.25 (dd, 2H); 7.35 (d, 1H); 7.60 (d, 1H); 10.90 (s, 1H); 11.10 (s, 1H). MS m/z (%): 345 (MH+, 5%), 199 (13%), 144 (54%), 107 (9%).

1f, 1-(3-(1H-indol-3-yl)-1-propyl)-4-(1H-indol-4-yl)piperazine, oxalate.

Mp 198–204° C. $^1$H NMR (DMSO-$d_6$): 2.05 (qv, 2H); 2.75 (t, 2H); 3.15 (t, 2H); 3.35 (s, 8H); 6.45 (s, 1H); 6.50 (d, 1H); 7.00 (t, 2H); 7.10 (t, 2H); 7.20 (d. 1H); 7.25 (t, 1H); 7.35 (d, 1H); 7.55 (d, 1H); 10.85 (b, 1H); 11.15 (b, 1H).

1g, 1-(4-(1H-indol-3-yl)-1-butyl)-4-(1H-indol-4yl)piperazine, oxalate.

Mp 189–93° C. $^1$H NMR (DMSO-$d_6$): 1.60–1.85 (m, 4H); 2.75 (t, 2H); 3.05 (t, 2H); 3.15–3.50 (m, 8H); 6.45 (s, 1H); 6.50 (s, 1H); 6.90–7.20 (m, 5H); 7.30 (s, 1H); 7.35 (d, 1H); 7.55 (d, 1H); 8.20 (b, 2H); 10.90 (s, 1H); 11.20 (s, 1H).

1h, 1-(3-(5-Fluoro-3-benzofuranyl)-1-propyl)-4-(1H-indol-4-yl)piperazine, dihydrochloride.

Mp 230–34° C. $^1$H NMR (DMSO-$d_6$): 2.20 (qv, 2H); 2.75 (t, 2H); 3.20–3.30 (m, 2H); 3.30–3.45 (m, 4H); 3.55–3.80 (m, 4H); 6.55 (s, 1H); 6.65 (d, 1H); 7.00 (t, 1H); 7.10–7.20 (m, 2H); 7.30 (t, 1H); 7.50–7.65 (m, 2H); 7.95 (s, 1H); 11.25 (s, 1H); 11.40 (b, 1H). MS m/z (%): 378 (MH+, 70%), 220 (26%), 199 (25%), 177 (18%), 159 (100%).

1i, 1-(2-(2-Methyl-4,5,6,7-tetrafluoro-3-benzofuranyl)ethyl)-4-(1H-indol-4-yl)piperaziine, dihydrochloride.

Mp 181–87° C. $^1$H NMR (DMSO-$d_6$): 2.50 (s, 3H); 3.15–3.50 (m, 8H); 3.65–3.85 (m, 4H); 6.50 (s, 1H); 6.60 (t, 1H); 7.05 (t, 1H); 7.15 (d, 1H); 7.35 (d, 11.20 (s, 1H); 11.75 (b, 1H). MS m/z (%): 414 (MH+–F, 13%), 396 (11%), 214 (72%), 199 (23%), 195 (34%), 159 (26%).

1j, 1-(2-(3-Indazolyl)ethyl)-4-(1H-indol-4-yl)piperazine, oxalate.

Mp 149–51° C. $^1$H NMR (DMSO-$d_6$): 3.05–3.15 (m, 4H); 3.15–3.20 (m, 2H); 3.20–3.35 (m, 6H); 6.40 (s, 1H); 6.50 (d, 1H); 7.00 (t, 1H); 7.05 (d, 1H); 7.10 (d, 1H); 7.25 (s, 1H); 7.35 (t, 1H); 7.50 (d, 1H); 7.80 (d, 1H); 11.10 (s, 1H). MS m/z (%): 346 (MH+, 40%); 199 (80%); 144 (100%).

1k, 1-(2-(6-Chloro-3-indazolyl)ethyl)-4-(1H-indol-4-yl)piperazine, oxalate.

Mp 255–58° C. $^1$H NMR (DMSO-$d_6$): 3.10–3.15 (m, 4H); 3.15–3.20 (m, 2H); 3.20–3.30 (m, 6H); 6.40 (s, 1H); 6.50 (d, 1H); 7.00 (t, 1H); 7.10 (d, 1H); 7.15 (d, 1H); 7.25 (s, 1H); 7.55 (s, 1H); 7.85 (d, 1H);). MS m/z (%): 380 (MH+, 100%), 214 (30%), 139 (50%).

11 , 1-(2-(7-Cyano-1H-indol-3-yl)ethyl)-4-(1H-indol-4-yl)piperazine, oxalate.

Mp 241–43° C. $^1$H NMR (DMSO-$d_6$): 3.15 (t, 2H); 3.30 (t, 2H); 3.30–3.50 (m, 8H); 6.45 (s, 1H); 6.50 (d, 1H); 7.00 (t, 1H); 7.10 (d, 1H); 7.20 (t, 1H); 7.30 (s, 1H); 7.50 (s, 1H); 7.60 (d, 1H); 8.00 (d, 1H); 11.15 (s, 1H); 11.90 (s, 1H). MS m/z (%): 370 (MH+, 100%), 214 (28%), 156 (42%).

Example 2

2a. 1-(2-(6-Chloro-1H-indol-3-yl)ethyl)-4-(1H-indol-4-yl)piperazine, oxalate.

A solution of 6-chloro-1H-indole (15 g) in diethyl ether (300 mL) was cooled to 0° C. and treated with a solution of oxalyl chloride (9.4 mL) in diethyl ether (30 mL). The mixture was stirred for 16 hours at room temperature. Filtration gave 2-(6-chloro-1H-indol-3-yl)-2-oxoacetyl chloride as a crystalline material (15.5 g). A part of this product (2.5 g) was dissolved in dry tetrahydrofuran (25 mL) and added dropwise to a solution of 1-(1H-indol-4-yl)piperazine (1.4 g) and triethylamine (15 mL) in tetrahydrofuran (100 mL). After stirring for 16 hours the reaction mixture was concentrated in vacuo. The remaining oil was purified by flash chromatography (eluent: ethyl acetate/methanol/triethylamine 85:10:5) giving 1-(2-(6-chloro-1H-indol-3-yl)-1,2-dioxoethyl)-4-(1H-indol-4-yl)piperazine (1.6 g) as a crystalline material. This product was suspended in tetrahydrofuran (25 mL) and added dropwise to a suspension of lithium aluminium hydride (1.5 g) in tetrahydrofuran (50 mL). The mixture was refluxed for 4 hours and cooled to 0° C. followed by subsequent addition of water (3 mL), 15% aq. sodium hydroxide (1.5 mL), and water (7.5 mL). Filtration and standard work-up gave a yellow oil which was converted to the title oxalate salt (1.5 g) from an acetone solution by addition of oxalic acid. Mp 229–31° C. $^1$H NMR (DMSO-$d_6$): 3.10 (t, 2H); 3.25–3.55 (m, 10H); 6.45 (s, 1H); 6.50 (d, 1H); 6.90–7.10 (m, 3H); 7.25–7.35 (m, 2H); 7.45 (s, 1H); 7.65 (d, 1H); 11.12 (s, 2H), MS m/z (%): 379 (MH+, 18%), 214 (16%), 199 (17%), 178 (16%), 143 (13%).

The following compounds were prepared analogously:

2b, 1-(2-(4-Chloro-1H-indol-3-yl)ethyl)-4-(1H-indol-4-yl)piperazine, oxalate.

Mp 245–47° C. $^1$H NMR (DMSO-$d_6$): 3.30–3.50 (m, 12H); 6.45 (s, 1H); 6.50 (d, 1H); 6.95–7.10 (m, 4H); 7.30 (s, 1H); 7.35–7.40 (m, 2H); 11.15 (s, 1H); 11.40 (s, 1H). MS m/z (%): 379 (NH+, 28%), 178 (41%), 143 (100%).

2c, 1-(2-(5-Fluoro-1H-indol-3-yl)ethyl)-4-(1H-indol-4-yl)piperazine, fumarate.

Mp 212–15° C. $^1$H NMR (DMSO-$d_6$): 2.75–3.10 (m, 8H); 3.10–3.35 (m, 4H); 6.40 (s, 1H); 6.50 (d, 1H); 6.60 (s, 2H); 6.85–7.10 (m, 3H); 7.20–7.40 (m, 4H); 10.95 (s, 1H); 11.05 (s, 1H). MS m/z (%): 363 (MH+, 18%), 214 (100%), 202 (34%), 199 (19%), 171(12%), 162 (87%).

2g, 1-(2-(6-Chloro-1H-indol-3-yl)ethyl)-4-(1H-indol-4-yl)-1,2,3,6-tetrahydropyridine, 1.5 fumarate.

Mp 225–26° C. $^1$H NMR (DMSO-$d_6$): 2.60–2.70 (m, 2H); 2.85–3.10 (m,6H); 3.40–3.50 (m, 2H); 6.10 (s, 1H); 6.60 (s, 3H); 6.90–7.10 (m, 3H), 7.20–7.40 (m, 3H); 7.40 (d, 1H); 7.60 (d, 1H); 11.05 (s, 1H); 11.15 (s, 1H). MS m/z (%): 376 (MH+, 12%), 179 (80%), 143 (100%).

2h, 1-(2-(5-Fluoro-1H-indol-3-yl)ethyl)-4-(1H-indol-4-yl)-1,2,3,6-tetrahydropyridine, trifumarate.

Mp 204–6° C. $^1$H NMR (DMSO-$d_6$): 2.70–2.85 (m, 2H); 3.00–3.20 (m, 4H); 3.25 (t, 2H); 3.70–3.80 (m, 2H); 6.05–6.15 (m, 1H); 6.60 (s, 6H); 6.85–7.00 (m, 2H); 7.10 (t, 1H); 7.30–7.45 (m, 6H); 11.00 (s, 1H); 11.20 (s, 1H). MS m/z (%): 360 (MH+), 162 (100%).

2i, 1-(2-(7-Bromo-1H-indol-3-yl)ethyl)-4-(1H-indol-4-yl)piperazine, hemioxalate.

Mp 149–51° C. $^1$H NMR (DMSO-$d_6$): 2.95–3.20 (m, 8H); 3.20–3.40 (m, 4H); 6.40 (s, 1H); 6.50 (d, 1H); 7.00 (dt, 2H); 7.10 (d, 1H); 7.25 (t, 1H); 7.30–7.40 (m, 2H); 7.60 (d, 1H); 11.05 (s, 1H); 11.10 (s, 1H). MS m/z (%): 423 (MH+, 9%), 222 (20%), 214 (29%), 143 (100%).

2j, 1-(1-Allyl-1H-indol-4-yl)-4-2-(6-chloro-1H-indol-3-yl)ethyl)piperazine, fumarate.

Mp 230–32° C. $^1$H NMR (DMSO-$d_6$): 2.70–3.00 (m, 8H); 3.10–3.30 (m, 4H); 4.75 (d, 2H); 5.00 (d, 1H); 5.15 (d, 1H); 5.85–6.05 (m, 1H); 6.40 (d, 1H); 6.55 (dd, 1H); 6.60 (s, 2H); 6.95–7.10 (m, 3H); 7.20–7.30 (m, 2H); 7.40 (d, 1H); 7.55 (d, 1H). MS m/z (%): 419 (MH+, 13%), 254 (21%), 143 (100%).

2k, 1-(1-Allyl-1H-indol-4-yl)-4-(2-(5-fluoro-1H-indol-3-yl)ethyl)piperazine, 1.25 fumarate.

Mp 210–12° C. $^1$H NMR (DMSO-$d_6$): 2.75–3.00 (m, 8H); 3.10–3.30 (m, 4H); 4.80 (d, 2H); 5.00 (d, 1H); 5.15 (d, 1H); 5.90–6.10 (m, 1H); 6.40 (d, 1H); 6.50 (dd, 1H); 6.60 (s, 2H); 6.90 (dt, 1H); 7.00–7.10 (m, 1H); 7.20–7.40 (m, 4H); 10.95 (s, 1H). MS m/z (%): 403 (MH+, 25%), 239 (30%), 162 (100%).

2l, 1-(1-Benzyl-1H-indol-4-yl)-4-(2-(6-chloro-1H-indol-3-yl)ethlyl)piperazine, hemifumarate.

Mp 237–39° C. $^1$H NMR (DMSO-$d_6$): 2.65–2.85 (mn 6H); 2.90 (t, 2H); 3.10–3.25 (m, 4H); 5.40 (s, 2H); 6.45 (d, 1H); 6.50 (d, 1H); 6.60 (s, 1H); 6.95–7.10 (m, 3H); 7.15 (d, 1H); 7.20–7.35 (m, 5H); 7.35–7.45 (m, 2H); 7.60 (d, 1H), 11.00 (s, 1H). MS m/z (%): 469 MH+, 20%), 304 (32%), 289 (22%), 143 (100%).

2m, 1-(1-Benzyl-1H-indol-4-yl)-4-(2-(5-fluoro-1H-indol-3-yl)ethyl)piperazine, fumarate.

Mp 178–80° C. $^1$H NMR (DMSO-$d_6$): 2.70–3.00 (m, 8H); 3.10–3.30 (m, 4H); 5.40 (s, 2H); 6.45 (d, 1H); 6.50 (d, 1H); 6.60 (s, 2H); 6.90 (dt, 1H); 7.00 (d, 1H); 7.10 (d, 1H); 7.15 (d, 1H); 7.20–7.40 (m, 5H); 7.45 (d, 1H); 10.95 (s, 1H). MS m/z (%): 453 (MH+, 28%), 304 (39%), 162 (100%).

2n, 1-(1-Benzyl-1H-indol-4-yl)-4-(2-(5-bromo-1H-indol-3-ylethyl)piperazine, fumarate.

Mp 230–32° C. $^1$H NMR (DMSO-$d_6$): 2.75–3.05 (m, 8H); 3.10–3.35 (m, 4H); 5.45 (s, 2H); 6.45 (d, 1H); 6.50 (d, 1H); 6.60 (s, 2H); 7.00 (t, 1H); 7.10 (d, 1H); 7.10–7.20 (m, 2H); 7.20–7.40 (m, 5H); 7.40 (d, 1H); 7.80 (s, 1H); 11.05 (s, 1H). MS m/z (%): 513 (MH+, 14%), 304 (30%), 142 (100%).

2o, 1-(2-(6-Chloro-1H-indol-3-yl)ethyl)-4-(1-propargyl-1H-indol-4-yl)piperazine.

Mp 197–99° C. $^1$H NMR (DMSO-$d_6$): 2.70–2.95 (m, 6H); 3.00 (t, 2H); 3.20–3.40 (m, 5H); 4.85 (d, 2H); 6.50 (d, 1H); 6.65 (d, 1H); 7.00–7.30 (m, 5H); 7.35 (s, 1H); 7.55 (d, 1H); 8.00 (s, 1H). MS m/z (%): 417 (MH+, 15%), 252 (24%), 237 (17%), 143 (100%).

2p, 1-(2-(1H-Indol-3-yl)ethyl)-4-(1-propargyl-1H-indol-4-yl)piperazine, hemifumarate.

Mp 193–95° C. $^1$H NMR (DMSO-$d_6$): 2.60–2.85 (m, 6H); 2.90 (t, 2H); 3.10–3.25 (m, 4H); 3.35 (t, 1H); 5.00 (d, 2H); 6.45 (d, 1H); 6.55 (d, 1H); 6.60 (s, 1H); 6.90–7.25 (m, 5H); 7.25–7.40 (m, 2H); 7.55 (d, 1H), 10.75 (s, 1H). MS m/z (%): 383 (MH+, 44%), 252 (55%), 143 (100%).

2q, 1-(2-(5-Fluoro-1H-indol-3-yl)ethyl)-4-(1-propargyl-1H-indol-4-yl)piperazine.

Mp 153–55° C. $^1$H NMR (DMSO-$d_6$): 2.70–2.90 (m, 6H), 2.90–3.10 (m, 3H); 3.25–3.45 (m, 4H); 4.85 (d, 2H); 6.55 (d, 1H); 6.65 (d, 1H); 6.95 (dt, 1H); 7.00–7.35 (m, 6H); 8.00 (s, 1H). MS m/z (%): 401 (MH+, 48%), 237 (27%), 162 (81%), 115 (100%).

2r, 1-(2-(5-Bromo-1H-indol-3-yl)ethyl)-4-(1-propargyl-1H-indol-4-yl)piperazine.

Mp 154–56° C. $^1$H NMR (DMSO-$d_6$): 2.70–2.90 (m, 6H); 2.90–3.00 (m, 3H); 3.25–3.40 (m, 4H); 4.85 (d, 2H); 6.55 (d, 1H); 6.65 (d, 1H); 7.00–7.10 (m, 2H); 7.10–7.35 (m, 4H); 7.75 (s, 1H); 8.05 (s, 1H). MS m/z (%): 461 (MH+, 5%), 252 (16%), 237 (12%), 143 (100%).

2s, 1-(1-Benzyl-1H-indol-4-yl)-4-(2-(1H-indol-3-yl)ethyl)piperazine, hemifumarate.

Mp 188–90° C. $^1$H NMR (DMSO-$d_6$): 2.65–2.85 (m, 6H); 2.95 (t, 2H); 3.10–3.30 (m, 4H); 5.45 (s, 2H); 6.45 (d, 1H); 6.50 (d, 1H); 6.60 (s, 1H); 6.90–7.10 (m, 4H); 7.10–7.35 (m, 7H); 7.40 (d, 1H); 7.55 (d, 1H); 10.80 (s, 1H). MS m/z (%): 435 (MH+, 22%), 304 (52%), 143 (100%).

2t, 1-(2-(5-Bromo-1H-indol-3-yl)ethyl)-4-(1H-indol-5-yl)piperazine, fumarate.

Mp 231–33° C. $^1$H NMR (DMSO-$d_6$): 2.80 (t, 2H); 2.80–2.90 (m, 4H); 2.95 (t, 2H); 3.10–3.20 (m, 4H); 6.30 (s, 1H); 6.60 (s, 2H); 6.85 (dd, 1H); 7.05 (s, 1H); 7.20 (dd, 1H); 7.25 (t, 1H); 7.25–7.30 (m, 2H); 7.35 (d, 1H); 7.75 (s, 1H); 10.80 (s, 1H); 11.05 (s, 1H). MS m/z (%): 425 (MH+, 11%), 223 (14%), 143 (100%).

2u, 1-(2-(5-Chloro-1H-indol-3-yl)ethyl)-4-(1H-indol-5-yl)piperazine, hemifumarate.

Mp 232–34° C. $^1$H NMR (DMSO-$d_6$): 2.70 (t, 2H); 2.70–2.80 (m, 4H); 2.90 (t, 2H); 3.05–3.15 (m, 4H); 6.30 (s, 1H); 6.60 (s, 1H); 6.85 (dd, 1H); 7.00 (s, 1H); 7.05 (d, 1H); 7.25 (t, 1H); 7.25–7.30 (m, 2H); 7.35 (d, 1H); 7.60 (s, 1H); 10.80 (s, 1H); 11.00 (s, 1H). MS m/z (%): 379 (MH+, 18%), 143 (100%).

Example 3

3a. 1-(2-(5-Fluoro-1H-indol-3-yl)ethyl)-4-(6-hydroxymethyl-1H-indol-4-yl)piperazine.

A solution of 1-(2-(5-fluoro-1H-indol-3-yl)-1,2-dioxoethyl)-4-(6-methoxycarbonyl-1H-indol-4-yl)piperazine (1.8 g, prepared from 2-(5-fluoro-1H-indol-3-yl)-2-oxoacetyl chloride and 1-(6-methoxycarbonyl-1H-indol-4-yl)piperazine by the procedure described in Example 2) in tetrahydrofuran (50 mL) was added dropwise to a suspension of lithium aluminium hydride (1.7 g) in tetrahydrofuran (125 mL) at room temperature followed by reflux for 4 hours. The reaction mixture was cooled to 5° C. followed by subsequent addition of water (3.4 mL), 15% aq. sodium hydroxide (1.7 mL), and water (8.5 mL). Filtration and removal of solvent in vacuo gave an oil which was purified by flash chromatography (eluent: ethyl acetate/methanol/triethylamine 85:10:5) giving the title product (0.9 g), which was crystallized from diisopropyl ether. Mp 198–200° C. $^1$H-NMR (DMSO-$d_6$): 2.60–2.80 (m, 6H); 2.85 (t, 2H); 3.15 (s, 4H); 4.45–4.55 (m, 2H); 4.90–5.00 (m, 1H); 6.30 (s, 1H); 6.40 (s, 1H); 6.90 (dd, 1H); 7.00 (s, 1H); 7.20 (s, 1H); 7.25–7.35 (m, 3H); 10.85 (s, 1H); 10.95 (s, 1H).

The following compounds were prepared analogously:

3b, 1-(2-(6-Chloro-1H-indol-3-yl)ethyl)-4-(6-hydroxymethyl-1H-indol-4-yl)piperazine.

Mp 194–96° C. $^1$H-NMR (DMSO-$d_6$): 2.60–2.80 (m, 6H); 2.90 (t, 2H); 3.1–3.20 (m, 4H); 4.50 (d, 2H), 4.95 (t, 1H), 6.35 (s, 1H); 6.45 (s, 1H); 6.95–7.05 (m, 1H); 7.20 (t, 1H), 7.25 (d, 1H), 7.35 (d, 1H); 7.55 (d, 1H); 10.95 (s, 2H).

3c, 1-(2-(5-Bromo-1H-indol-3-yl)ethyl)-4-(6-hydroxymethyl-1H-indol-4-yl)piperazine.

Mp 163–65° C. $^1$H-NMR (DMSO-$d_6$): 2.65 (t, 2H); 2.70 (s, 4H); 2.90 (t, 2H); 3.15 (s, 4H); 4.50 (d, 2H); 4.95 (t, 1H); 6.35 (s, 1H); 6.45 (s, 1H); 7.00 (s, 1H); 7.10–7.20 (m, 2H); 7.25 (s, 1H); 7.30 (d, 1H); 7.70 (s, 1H); 10.90 (s, 1H); 11.00 (s, 1H).

Example 4

4a, 1-(3-(6-Fluoro-1,2-benzisoxazol-3-yl)-1-propyl)-4-(1H-indol-4-yl)piperazine, fumarate.

A solution of 3-(3-bromo-1-propyl)-6-fluoro-1,2-benzisoxazole (1.1 g), 1-(1H-indol-4-yl)piperazine (1.0 g), potassium carbonate (1.9 g), and potassium iodide (50 mg) in 4-methyl-2-pentanone (100 mL) was refluxed for 16 hours. Filtration and removal of solvent in vacuo gave an oil which was purified by flash chromatography (eluent: heptane/ethyl acetate/triethylamine 75:20:5) giving an oil (1.0 g) which was crystallized as the title fumarate from acetone by addition of fumaric acid. Mp 187–89° C. $^1$H NMR (DMSO-$d_6$): 2.00 (qv, 2H); 2.55 (t, 2H); 2.60–2.80 (m, 4H); 3.05 (t, 2H); 3.05–3.20 (m, 4H); 6.40 (s, 1H); 6.45 (d, 1H); 6.60 (s, 2H); 6.90–7.05 (m, 2H); 7.20–7.35 (m, 2H); 7.70 (dd, 1H); 8.00 (dd, 1H); 11.00 (s, 1H). MS m/z (%): 379 (MH+, 10%), 178 (100%), 159 (24%).

The following compounds were prepared analogously:

4f, 1-(2-(1H-indol-3-yl)ethyl)-4-(6-methoxycarbonyl-1H-indol-4-yl)piperazine, oxalate.

Mp 213–16° C. $^1$H-NMR DMSO-$d_6$): 3.10 (t, 2H); 3.20–3.60 (m, 10H); 3.80 (s, 3H); 6.55 (s, 1H); 6.90–7.10 (m, 3H); 7.25 (s, 1H); 7.35 (d, 1H); 7.50 (s, 1H); 7.60 (d, 1H); 7.75 (s, 1H); 10.90 (s, 1H); 11.55 (s, 1H).

4g, 1-(2-(6-Chloro-1H-indol-3-yl)ethyl)-4-(6-methoxycarbonyl-1-H-indol-4-yl)piperazine, oxalate.

Mp 228–30° C. $^1$H-NMR (DMSO-$d_6$): 3.10 (t, 2H); 3.30 (t, 2H); 3.45 (s, 8H); 3.85 (s, 3H); 6.55 (s, 1H); 7.05 (dd, 1H); 7.10 (s, 1H); 7.33 (d, 1H); 7.45 (s, 1H); 7.55 (t, 1H); 7.65 (d, 1H); 7.85 (s, 1H); 11.15 (s, 1H); 11.65 (s, 1H).

4h, 1-(2-(5-Fluoro-3-benzofuranyl)ethyl)-4-(6-methoxycarbonyl-1H-indol-4-yl)piperazine, oxalate.

Mp 227–28° C. $^1$H-NMR (DMSO-$d_6$): 3.05 (t, 2H); 3.25 (t, 2H); 3.25–3.35 (m, 4H); 3.35–3.45 (m, 4H); 3.85 (s, 3H); 6.55 (s, 1H); 7.10 (s, 1H); 7.15 (t, 1H); 7.55 (t, 1H); 7.55–7.65 (m, 2H); 7.80 (s, 1H); 8.00 (s, 1H); 11.55 (s, 1H).

4l, 1-(5-Fluoro-3-benzofuranylmethyl)-4-(1H-indol-4-4-yl)piperazine, dihydrochloride.

Mp 238–40° C. $^1$H NMR (DMSO-$d_6$): 3.20–3.50 (m. 4H); 3.60 (d, 2H); 3.75 (d, 2H); 4.60 (s, 2H); 6.50 (s, 1H); 6.55 (d, 1H); 7.00 (t, 1H); 7.15 (d, 1H); 7.25 (dt, 1H); 7.25–7.30 (m, 1H); 7.70 (dd, 1H); 8.00 (dd, 1H); 8.40 (s, 1H); 11.22 (s, 1H); 11.65 (b, 1H). MS m/z (%): 350 (MH+, 7%), 201 (34%), 159 (100%), 149 (20%).

4m, 1-(3-Cyano-1H-indol-4-yl)-4-(2-(1H-indol-3-yl)ethyl)piperazine, fumarate.

Mp >250° C. $^1$H NMR (DMSO-$d_6$): 2.70–3.00 (m, 8H); 3.10 (s, 4H); 6.60 (s, 1H); 6.75 (dd, 1H); 6.95–7.10 (m, 2H); 7.15–7.20 (m, 3H); 7.35 (d, 1H); 8.20 (s, 1H); 10.80 (s, 1H); 12.20 (s, 1H). MS m/z (%): 370 (MH+, 9%), 239 (100%), 227 (25%), 224 (27%), 144 (65%).

4n, 1-(3-Cyano-1H-indol-4-yl)-4-(2-(5-fluoro-3-benzofuranyl)ethyl)piperazine, hemifumarate.

Mp 235–37° C. $^1$H NMR (DMSO-$d_6$): 2.60–2.95 (m, 8H); 3.10 (s, 4H); 6.60 (s, 2H); 6.75 (d, 1H); 7.05–7.25 (m, 3H); 7.45–7.60 (m, 2H); 7.95 (s, 1H); 8.20 (s, 1H); 12.15 (s, 1H). MS m/z (%): 389 (MH+, 8%), 239 (100%), 224 (38%), 208 (14%), 163 (15%).

4o, 1-(2-(6-Chloro-1H-indol-3-yl)ethyl)-4-(3-cyano-1H-indol-4-yl)piperazine, hemifumarate.

Mp 234–36° C. $^1$H NMR (DMSO-$d_6$):2.70 (t, 2H); 2.80 (b, 4H); 2.90 (t, 2H); 3.10 (b, 4H); 6.60 (d, 2H); 6.75 (d, 1H); 7.00 (d, 1H); 7.15–7.20 (m, 2H); 7.25 (s, 1H); 7.35 (s, 1H); 7.55 (d, 1H); 8.20 (s, 1H); 10.90 (s, 1H); 12.10 (s, 1H). MS m/z (%): 404 (MH+, 8%), 239 (100%), 227 (18%), 224 (30%), 178 (25%).

4p, 1-(2-(3-Benzofuranyl)ethyl)-4-(3-cyano-1H-indol-4-yl)piperazine, sesquioxalate.

Mp 221–23° C. $^1$H NMR (DMSO-$d_6$): 3.10 (t, 2H); 3.20–3.45 (m, 10H); 6.80 (d, 1H); 7.15–7.40 (m, 4H); 7.60 (dd, 1H); 7.75 (dd, 1H); 7.90 (s, 1H); 8.25 (d, 1H); 12.30 (s, 1H). MS m/z (%): 371 (MH+, 20), 239 (63%), 145 (100%).

4q, 1-(1H-Indol-4-yl)-4-(2-(5-methyl-3-benzofuranyl)ethyl)piperazine, hydrochloride.

Mp 258–60° C. $^1$H NMR (DMSO-$d_6$):2.40 (s, 3H); 3.15–3.55 (m, 8H); 3.65–3.80 (m, 4H); 6.50 (d, 1H); 6.60 (d, 1H); 7.00 (t, 1H); 7.15 (d, 1H); 7.20 (d, 1H); 7.30 (t, 1H); 7.45 (d, 1H); 7.60 (s, 1H); 7.90 (s, 1H); 11.20 (s, 1H). MS m/z (%): 360 (NMH+, 10%), 214 (97%), 143 (100%).

4r, 1-(1H-Indol-4-yl)-4-(2-(4-methyl-3-benzofuranyl)ethyl)piperazine, oxalate.

Mp 204–6° C. $^1$H NMR (DMSO-$d_6$): 2.05 (s, 3H); 3.30–3.50 (m, 12H); 6.45 (d, 1H); 6.50 (d, 1H); 6.95–7.05 (m, 2H); 7.10 (d, 1H); 7.20 (t, 1H); 7.30 (t, 1H); 7.40 (d, 1H); 7.85 (s, 1H); 11.10 (s,1H).). MS m/z (%): 360 (MH+, 23%), 214 (81%), 199 (100%), 143 (53%).

4s, 1-(3-(5-Fluoro-3-benzofuranyl)-1-propyl)-4-(1H-indol-4-yl)-1,2,3,6-tetrahydropyridine, fumarate.

Mp 183–85° C. $^1$H NMR (DMSO-$d_6$):1.70–2.00 (m, 2H); 2.40–2.90 (m, 8H); 3.20–3.35 (m, 2H); 6.00–6.10 (m, 1H); 6.55 (s, 1H); 6.60 (s, 2H); 6.90 (d, 1H); 7.05 (t, 1H); 7.15 (dt, 1H); 7.25–7.40 (m, 2H); 7.50 (dd, 1H); 7.55 (dd, 1H); 7.90 (s, 1H); 11.10 (s, 1H). MS m/z (%): 375 (MH+, 90%), 206 (100%), 149 (90%).

4t, 1-(2-(5-Chloro-3-benzofuranyl)ethyl)-4-(1H-indol-4-yl)piperazine, oxalate.

Mp 200–2° C. $^1$H NMR (DMSO-$d_6$): 3.10 (t, 2H); 3.30–3.50 (m, 10H); 6.45 (d, 1H); 6.50 (d, 1H); 7.00 (t, 1H); 7.10 (d, 1H); 7.30 (t, 1H); 7.40 (dd, 1H); 7.65 (d, 1H); 7.90

(s, 1H); 8.00 (s, 1H); 11.10 (s, 1H). MS m/z (%): 380 (MH+, 50%), 214 (100%), 143 (80%).

4u, 1-(1H-Indol-4-yl)-4-(2-(6-methyl-3-benzofuranyl)ethyl) piperazine, oxalate.

Mp 190–92° C. $^1$H NMR (DMSO-d$_6$): 2.10 (s, 3H); 3.10 (t, 2H); 3.25–3.50 (m, 10H); 6.45 (d, 1H); 6.50 (d, 1H); 7.00 (t, 1H); 7.10 (t, 2H); 7.30 (t, 1H); 7.40 (s, 1H); 7.65 (d, 1H); 7.80 (s, 1H); 11.15 (s, 1H). MS m/z (%): 360 (MH+, 14%), 214 (44%),143 (100%).

4v, 1-(2-(7-Chloro-3-benzofuranyl)ethyl)-4-(1H-indol-4-yl) piperazine, hemioxalate.

Mp 216–18° C. $^1$H NMR (DMSO-d$_6$): 2.85–3.15 (m, 8H); 3.15–3.40 (m, 4H); 6.40 (d, 1H); 6.50 (d, 1H); 7.00 (t, 1H); 7.05 (d, 1H); 7.25 (t, 1H); 7.30 (d, 1H); 7.45 (d, 1H); 7.75 (d, 1H); 8.00 (s, 1H); 11.05 (s, 1H). MS m/z (%): 380 (MH+, 13%), 199 (30%), 143 (100%).

4x, 1-(2-(4-Chloro-1H-indol-3-yl)ethyl)-4-(3-cyano-1H-indol-4-yl)piperazine, hemifumarate.

Mp >250° C. $^1$H NMR (DMSO-d$_6$): 2.65–3.00 (m, 6H); 3.00–3.30 (m, 6H); 6.60 (s, 1H); 6.75 (dd, 1H); 6.90–7.10 (m, 2H); 7.10–7.25 (m, 2H); 7.25–7.40 (m, 2H); 8.20 (d, 1H); 11.20 (s, 1H); 12.10 (s, 1H). MS m/z (%): 404 (MH+, 14%), 224 (15%), 184 (18%), 143 (100%).

Example 5

5a, 1-(2-(6-Chloro-1H-indol-3-yl)-4-(1H-indol-4-yl) piperidine.

A solution of compound 2 g (0.5 g) was dissolved in glacial acetic acid. Platinum catalyst (10% on charcoal, 10 mg) was added and the mixture hydrogenated in a Parr apparatus under 3 atmospheres of hydrogen gas for 16 hours. Filtration and removal of solvent gave the title compound as a crystalline material (0.4 g). Mp 205–6° C. $^1$H NMR (DMSO-d6):1.75–1.90 (m, 4H); 2.10–2.20 (m, 2H); 2.60–2.70 (m, 2H); 2.85–2.95 (m, 3H); 3.15 (d, 2H); 6.50 (s, 1H); 6.80–6.90 (m, 2H); 6.95–7.10 (m, 2H); 7.20 (s, 1H); 7.30 (s, 1H); 7.40 (s, 1H); 7.55 (d, 1H); 10.90 (s, 1H); 11.00 (s, 1H). MS m/z (%): 378 (MH+, 18%), 178 (100%), 143 (47%).

Pharmacological Testing

The affinity of the compounds of the invention to 5-HT$_{1A}$ receptors was determined by measuring the inhibition of binding of a radioactive ligand at 5-HT$_{1A}$ receptors as described in the following test:

Inhibition of $^3$H-5-CT Binding to Human 5HT$_{1A}$ Receptors

By this method the inhibition by drugs of the binding of the 5-HT$_{1A}$ agonist $^3$H-5-carboxamido tryptamine ($^3$H-5-CT) to cloned human 5-HT$_{1A}$ receptors stably expressed in transfected HeLa cells (HA7) (Fargin, A. et al, *J. Biol. Chem.*, 1989, 264, 14848) is determined in vitro. The assay was performed as a modification of the method described by Harrington, M. A. et al, *J. Pharmacol. Exp. Ther.*, 1994, 268, 1098. Human 5-HT$_{1A}$ receptors (40 μg of cell homogenate) were incubated for 15 minutes at 37° C. in 50 mM Tris buffer at pH 7.7 in the presence of $^3$H-5-CT. Non-specific binding was determined by including 10 μM of metergoline. The reaction was terminated by rapid filtration through Unifilter GF/B filters on a Tomtec Cell Harvester. Filters were counted in a Packard Top Counter. The results obtained are presented in table 1:

TABLE 1

| Compound No. | Inhibition of $^3$H-5-CT Binding IC$_{50}$ (nM) |
|---|---|
| 1a | 10 |
| 1b | 210 |
| 1c | 12 |
| 1d | 2.5 |
| 1e | 6.9 |
| 1f | 9.8 |
| 1g | 13 |
| 1h | 11 |
| 1i | 3.4 |
| 1j | 22 |
| 1k | 22 |
| 1l | 2.5 |
| 2a | 3.4 |
| 2b | 11 |
| 2c | 27 |
| 2g | 2.8 |
| 2h | 11 |
| 2i | 5.4 |
| 2t | 230 |
| 2u | 310 |
| 3a | 910 |
| 3b | 120 |
| 3c | 1000 |
| 4a | 9.8 |
| 4f | 1200 |
| 4g | 350 |
| 4h | 3100 |
| 4l | 330 |
| 4m | 3.2 |
| 4n | 5.7 |
| 4o | 2.9 |
| 4p | 4.3 |
| 4q | 21 |
| 4r | 10 |
| 4s | 16 |
| 4t | 9.4 |
| 4u | 7.0 |
| 4v | 4.3 |
| 4x | 5.4 |
| 5a | 14 |
| Pindolol* | 100 |

*reference compound

The compounds of the invention have also been tested for their effect on re-uptake of serotonin in the following test:

Inhibition of $^3$H-5-HT Uptake Into Rat Brain Synaptosomes

Using this method the ability of drugs to inhibit the accumulation of $^3$H-5-HT into whole rat brain synaptosomes is determined in vitro. The assay was performed as described by Hyttel, J., *Psychopharmacology* 1978, 60, 13.

TABLE 1

| Compound No. | Inhibition of Serotonin reuptake IC$_{50}$ (nM) |
|---|---|
| 1a | 31 |
| 1b | 290 |
| 1c | 57 |
| 1d | 31 |
| 1e | 4.4 |
| 1f | 8.2 |
| 1g | 12 |
| 1h | 6.8 |
| 1i | nt |
| 1j | 360 |
| 1k | 150 |

TABLE 1-continued

| Compound No. | Inhibition of Serotonin reuptake IC$_{50}$ (nM) |
|---|---|
| 1l | nt |
| 2a | 21 |
| 2b | 6.9 |
| 2c | 2.3 |
| 2g | 22 |
| 2h | 2.5 |
| 2i | 5.9 |
| 2t | 39 |
| 2u | 20 |
| 3a | 17 |
| 3b | 33 |
| 3c | 46 |
| 4a | 360 |
| 4f | 14 |
| 4g | 23 |
| 4h | 71 |
| 4l | 950 |
| 4m | 3.0 |
| 4n | 65 |
| 4o | 19 |
| 4p | 22 |
| 4q | 34 |
| 4r | 12 |
| 4s | 24 |
| 4t | 99 |
| 4u | 93 |
| 4v | 4.4 |
| 4x | nt |
| 5a | 19 |
| Paroxetine* | 0.29 |

*reference compound, nt =0 not tested

The 5-HT$_{1A}$ antagonistic activity of some of the compounds of the invention has been estimated in vitro at cloned 5-HT$_{1A}$ receptors stably expressed in transfected HeLa hells (HA7). In this test 5-HT$_{1A}$ antagonistic activity are estimated by measuring the ability of the compounds to antagonize the 5-HT induced inhibition of forskolin induced cAMP accumulation. The assay was performed as a modification of the method described by Pauwels, P. J. et al, *Biochem. Pharmacol.* 1993, 45, 375.

Some of the compounds of the invention have also been tested for their in vivo effect on 5-HT$_{1A}$ receptors in the assay described by Sanchez. C. Et al., *Eur. J. Pharmacol.*, 1996, 315, pp 245. In this test antagonistic effects of test compounds are determined by measuring the ability of the test compounds to inhibit 5-MeO-DMT induced 5-HT syndrome.

The compounds of the present invention possess valuable activity as serotonin re-uptake inhibitors and have antagonistic effect at 5-HT$_{1A}$ receptors. The compounds of the invention are therefore considered useful for the treatment of diseases and disorders responsive to the inhibition of serotonin re-uptake and antagonistic activity at 5-HT$_{1A}$ receptors. Diseases responsive to the inhibition of serotonin re-uptake are well known in the art and include affective disorders, such as depression, psychosis, anxiety disorders including general anxiety disorder and panic disorder, obsessive compulsive disorder, etc.

As explained above, the antagonistic activity at 5-HT$_{1A}$ receptors of the compounds of the invention is predicted to counteract the negative feed back mechanism induced by the inhibition of serotonin reuptake. The antagonistic effect at 5-HT$_{1A}$ receptors is thus expected to improve the effect of the serotonin reuptake inhibiting activity of the compounds of the invention.

The compounds as claimed herein are therefore considered to be particularly useful as fast onset of action medicaments for the treatment of depression. The compounds may also be useful for the treatment of depressions which are non-responsive to currently available SSRI's.

Pharmaceutical Formulation

The pharmaceutical formulations of the invention may be prepared by conventional methods in the art. For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients, or other additives normally used in the art may be used. Conveniently, the compounds of the invention are administered in unit dosage form containing said compounds in an amount of about 0.01 to 100 mg. The total daily dose is usually in the range of about 0.05–500 mg, and most preferably about 0.1 to 50 mg of the active compound of the invention.

What is claimed is:

1. A substituted 4-, 5-, 6-, or 7-indole or indoline derivative of Formula:

(I)

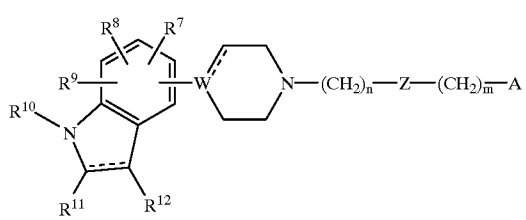

wherein W is N and the dotted lines indicate optional bonds and wherein A is a group having the formula:

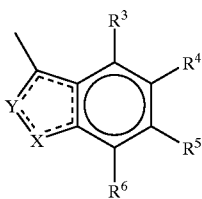

(IIA)

wherein
X is $CR^{1A}$, $CHR^{1A}$, N, $NR^{1B}$, O, or S, where $R^{1A}$ is as defined for $R^3$ to $R^9$ below, and where $R^{1B}$ is as defined for $R^{10}$ below;
Y is $CR^{2A}$, $CHR^{2A}$, N, $NR^{2B}$, O, or S, where $R^{2A}$ is as defined for $R^3$ to $R^9$ below and where $R^{2B}$ is as defined for $R^{10}$ below, and
the dotted lines indicate optional bonds;
provided that X and Y are not both O or S;
A is a group having the formula

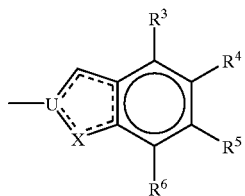

(IIB)

wherein
X is $CR^{1A}$, $CHR^{1A}$, N, $NR^{1B}$, O, or S, where $R^{1A}$ is as defined for $R^3$ to $R^9$ below, and where $R^{1B}$ is as defined for $R^{10}$ below;
U is C, CH, or N; and
the dotted lines indicate optional bonds; or
A is a group having the formula

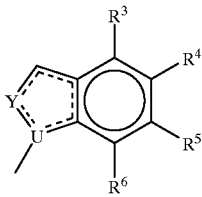

(IIC)

where
U is C, CH, or N;
Y is $CR^{2A}$, $CHR^{2A}$, N, $NR^{2B}$, O, or S, where $R^{2A}$ is as defied for $R^3$ to $R^9$ below and where $R^{2B}$ is as defined for $R^{10}$ below; and
the dotted lines indicate optional bonds;
n is 0, 1, 2, 3, 4, or 5, and m is 0, 1, 2, 3, 4, or 5;
Z is $CH_2$, O, S, CO, SO, or $SO_2$, provided that if n is 0 then Z is $CH_2$;
$R^3$–$R^9$ and $R^{11}$ to $R^{12}$ are independently selected from hydrogen, halogen, cyano, nitro, $C_{1-6}$-alkenyl, $C_{1-6}$ alkynyl, $C_{1-6}$ alkyl, $C_{1-6}$ alkoxy, $C_{1-6}$-alkylthio, hydroxy, hydroxy-$C_{1-6}$-alkyl, $C_{1-6}$-alkoxycarbonyl, $C_{3-8}$ cycloalkyl, $C_{3-8}$ cycloalkenyl, $C_{3-8}$-cycloalkyl-$C_{1-6}$-alkyl, $C_{3-8}$-cycloalkyl-$C_{1-6}$-alkenyl, $C_{3-8}$ cycloalkyl-$C_{1-6}$-alkynyl, $C_{3-8}$ cycloalkenyl-$C_{1-6}$-alkyl, $C_{3-8}$-cycloalkenyl-$C_{1-6}$ alkenyl, $C_{3-8}$-cycloalkenyl-$C_{1-6}$-alkynyl, $C_{1-6}$-alkylcarbonyl, phenylcarbonyl, halogen substituted phenylcarbonyl, trifluoromethyl, trifluoromethylsulfonyloxy, $C_{1-6}$ alkylsulfonyl, aryl and heteroaryl, or two adjacent groups taken from $R^3$–$R^9$ may together form a methylenedioxy group, or two adjacent groups $R^7$–$R^9$ may together form a cyclopentyl or cyclohexyl ring which may be substituted with one more methyl groups, or one of $R^7$–$R^9$ may alternatively be a group —$NR^{13}R^{14}$ wherein $R^{13}$ is as defined for $R^{10}$ below and $R^{14}$ is hydrogen, $C_{1-6}$-alkenyl, $C_{1-6}$ alkynyl, $C_{1-6}$ alkyl, $C_{3-8}$ cycloalkyl, $C_{3-8}$ cycloalkenyl, $C_{3-8}$-cycloalkyl-$C_{1-6}$-alkyl, $C_{3-8}$-cycloalkyl-$C_{1-6}$-alkenyl, $C_{3-8}$ cycloalkyl-$C_{1-6}$ alkynyl, $C_{3-8}$ cycloalkenyl-$C_{1-6}$-alkyl, $C_{3-8}$-cycloalkenyl-$C_{1-6}$ alkenyl, $C_{3-8}$-cycloalkenyl-$C_{1-6}$-alkynyl, aryl, heteroaryl, aryl-$C_{1-6}$ alkyl, or heteroaryl-$C_{1-6}$-alkyl;

$R^{10}$ is
hydrogen, $C_{1-6}$-alkyl, $C_{1-6}$-alkenyl, $C_{1-6}$-alkynyl, $C_{3-8}$-cycloalkyl, $C_{3-8}$-cycloalkenyl, $C_{3-8}$-cycloalkyl-$C_{1-6}$-alkyl, $C_{3-8}$-cycloalkyl-$C_{1-6}$-alkenyl, $C_{3-8}$-cycloalkyl $C_{1-6}$-alkynyl, $C_{3-8}$-cycloalkenyl $C_{1-6}$-alkyl, $C_{3-8}$-cycloalkenyl $C_{1-6}$-alkenyl, $C_{3-8}$-cycloalkenyl $C_{1-6}$-alkynyl, aryl, heteroaryl, aryl-$C_{1-6}$-alkyl, heteroaryl-$C_{1-6}$-alkyl, acyl, thioacyl, $C_{1-6}$-alkylsulfonyl, trifluoromethylsulfonyl, arylsulfonyl, or heteroarylsulfonyl;

$R^{15}VCO$— wherein V is O or S and $R^{15}$ is $C_{1-6}$-alkyl, $C_{1-6}$-alkenyl, $C_{1-6}$-alkynyl, $C_{3-8}$-cycloalkyl, $C_{3-8}$-cycloalkenyl, $C_{3-8}$-cycloalkyl-$C_{1-6}$-alkyl, $C_{3-8}$-cycloalkyl-$C_{1-6}$-alkenyl, $C$-$_{3-8}$-cycloalkyl $C_{1-6}$-alkynyl, $C_{3-8}$-cycloalkenyl $C_{1-6}$-alkyl, $C_{3-8}$-cycloalkenyl $C_{1-6}$-alkenyl, $C_{3-8}$-cycloalkenyl $C_{1-6}$-alkynyl, aryl, or heteroaryl; or a group $R^{16}R^{17}NCO$- or $R^{16}R^{17}NCS$— wherein $R^{16}$ and $R^{17}$ are independently selected from hydrogen, $C_{1-6}$-alkyl, $C_{1-6}$-alkenyl, $C_{1-6}$-alkynyl, $C_{3-8}$-cycoalkyl, $C_{3-8}$-cycloalkenyl, $C_{3-8}$-cycloalkyl-$C_{1-6}$-alkyl, $C_{3-8}$-cycloalkyl-$C_{1-6}$-alkenyl, $C_{3-8}$-cycloalkyl-$C_{1-6}$ alkynyl, $C_{3-8}$cycloalkenyl-$C_{1-6}$-alkyl, $C_{3-8}$-cycloalkenyl-$C_{1-6}$alkenyl, $C_{3-8}$-cycloalkenyl-$C_{1-6}$-alkynyl, heteroaryl, or aryl, or $R^{16}$ and $R^{17}$ together with the N-atom to which they are linked, form a pyrrolidinyl, piperidinyl, morpholinyl, or perhydroazepin group;

or an acid addition salt thereof.

2. A compound according to claim 1 wherein A is a group having the formula

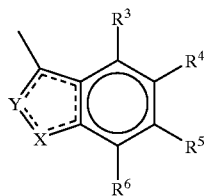

(IIA)

wherein X, Y, the dotted lines and $R^3$–$R^6$ are as defined in claim 1.

3. A compound according to claim 2 wherein A is a group having the formula

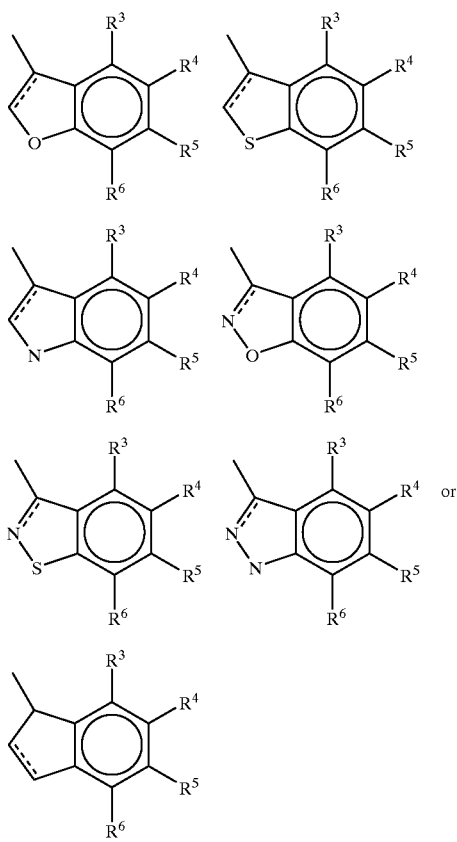

wherein $R^3$ to $R^6$ and the dotted lines are as defined in claim 2.

4. A compound according to claim 3 wherein A is a group having the formula

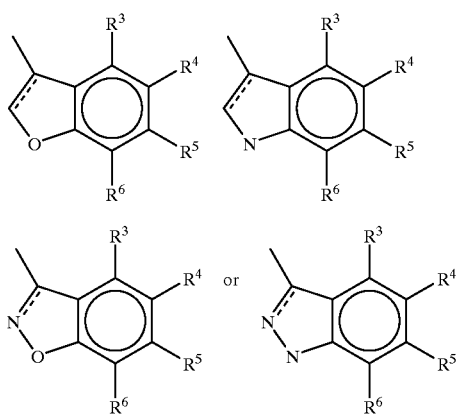

wherein $R^3$ to $R^6$ and the dotted lines are as defined in claim 3.

5. A compound according to claim 1 having the formula (II)

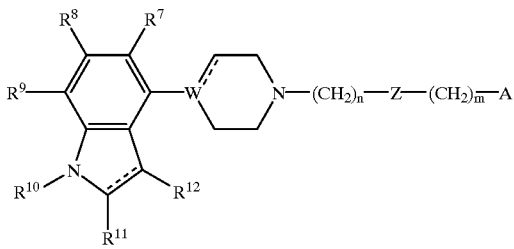

wherein $R^7$ to $R^{12}$, W, A, Z n, m and the dotted lines are as defined in claim 1.

6. A compound according to claim 1 wherein Z is $CH_2$ and n+m is 0, 1, 2, 3, 4, 5, or 6.

7. A compound according to claim 1 having the formula (II)

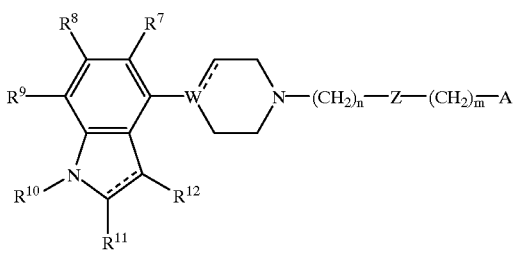

wherein $R^7$ to $R^{12}$, W, Z, n, m and the dotted lines are as defined in claim 1 and A is a group having the formula (IIA)

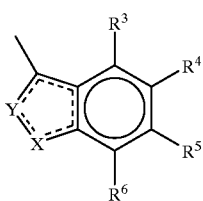

wherein X, Y, the dotted lines and $R^3$–$R^6$ is as defined in claim 1.

8. A compound according to claim 7 wherein A is a group having the formula

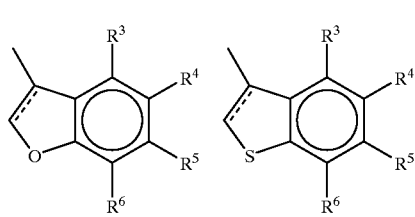

-continued

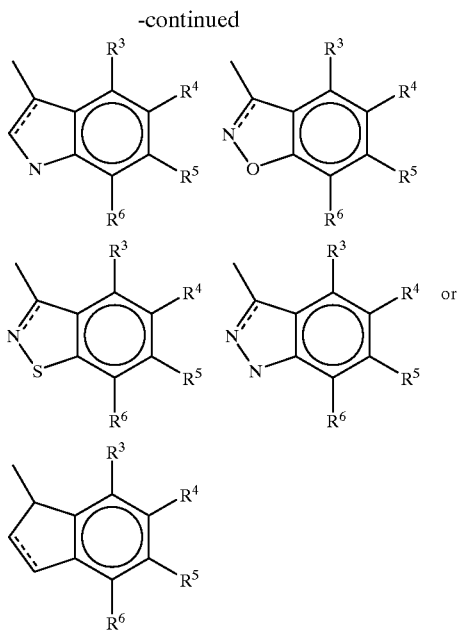

wherein $R^3$ to $R^6$ and the dotted line is as defined in claim 8.

9. A compound according to claim 8 wherein A is a group having the formula

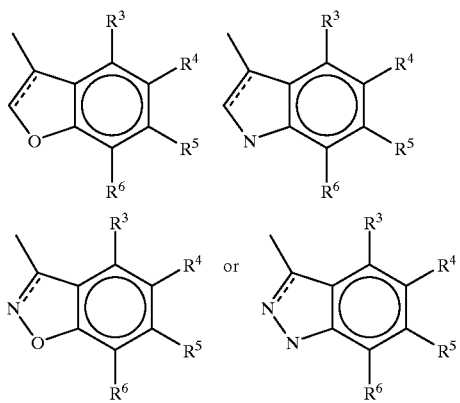

wherein $R^3$ to $R^6$ and the dotted line is as defined in claim 9.

10. A compound of claim 1 wherein Z is $CH_2$ and n+m is 0, 1, 2, 3, 4, 5, or 6 and $R^3$–$R^9$ and $R^{11}$–$R^{12}$ is hydrogen, halogen, cyano, nitro, $C_{1-6}$-alkyl, $C_{1-6}$-alkoxy hydroxy, hydroxy-$C_{1-6}$-alkyl, $C_{1-6}$-alkoxycarbonyl and trifluoromethyl; and $R^{10}$ is hydrogen.

11. A compound according to claim 1 which is
1-(2-(3-Benzofuranyl)ethyl)-4-(1H-indol-4-yl)piperazine,
1-(3-Benzofuranylmethyl)-4-(1H-indol-4-yl)piperazine,
1-(2-(5-Fluoro-3-benzofuranyl)ethyl)-4-(1H-indol-4-yl)piperazine,
1-(4-(5-Fluoro-3-benzofuranyl)-1-butyl)-4-(1H-indol-4-yl)piperazine,
1-(2-(1H-Indol-3-yl)ethyl)-4-(1H-indol-4-yl)piperazine,
1-(3-(1H-Indol-3-yl)-1-propyl)-4-(1H-indol-4-yl)piperazine,
1-(4-(1H-Indol-3-yl)-1-butyl)-4-(1H-indol-4-yl)piperazine,
1-(3-(5-Fluoro-3-benzofuranyl)-1-propyl)-4-(1H-indol-4-yl)piperazine,
1-(2-(2-Methyl-4,5,6,7-tetrafluoro-3-benzofuranyl)ethyl)-4-(1H-indol-4-yl)piperazine,
1-(2-(3-indazolyl)ethyl)-4-(1H-indol-4-yl)piperazine,
1-(2-(6-Chloro-3-indazolyl)ethyl)-4-(1H-indol-4-yl)piperazine,
1-(2-(7-Cyano-1H-indol-3-yl)ethyl)-4-(1H-indol-4-yl)piperazine,
1-(2-(6-Chloro-1H-indol-3-yl)ethyl)-4-(1H-indol-4-yl)piperazine,
1-(2-(4-Chloro-1H-indol-3-yl)ethyl)-4-(1H-indol-4-yl)piperazine,
1-(2-(5-Fluoro-1H-indol-3-yl)ethyl)-4-(1H-indol-4-yl)piperazine,
1-(2-(7-Bromo-1H-indol-3-yl)ethyl)-4-(1H-indol-4-yl)piperazine,
1-(1-Allyl-1H-indol-4-yl)-4-(2-(6-chloro-1H-indol-3-yl)ethyl)piperazine,
1-(1-Allyl-1H-indol-4-y)-4-(2-(5-fluoro-1H-indol-3-yl)ethyl)piperazine,
1-(1-Benzyl-1H-indol-4-yl)-4-(2-(6-chloro-1H-indol-3-yl)ethyl)piperazine,
1-(1-Benzyl-1H-indol-4-yl)-4-(2-(5-fluoro-1H-indol-3-yl)ethyl)piperazine,
1-(1-Benzyl-1H-indol-4-yl)-4-(2-(5-bromo-1H-indol-3-yl)ethyl)piperazine,
1-(2-(6-Chloro-1H-indol-3-yl)ethyl)-4-(1-propargyl-1H-indol-4-yl)piperazine,
1-(2-(1H-Indol-3-yl)ethyl)-4-(1H-propargyl-1H-indol-4-yl)piperazine,
1-(2-(5-Fluoro-1H-indol-3-yl)ethyl)-4-(l1-propargyl-1H-indol-4-yl)piperazine,
1-(2-(5-Bromo-1H-indol-3-yl)ethyl)-4-(l1-propargyl-1H-indol-4-yl)piperazine,
1-(1-Benzyl-1H-indol-4-yl)-4-(2-(1H-indol-3-yl) ethyl)piperazine,
1-(2-(5-Bromo-1H-indol-3-yl)ethyl)-4-(1H-indol-5-yl)piperazine,
1-(2-(5-Chloro-1H -indol-3-yl)ethyl)-4-(1H-indol-5-yl)piperazine,
1-(2-(5-Fluoro-1H-indol-3-yl)ethyl)-4-(6-hydroxymethyl-1H-indol-4-yl)piperazine,
1-(2-(6-Chloro-1H-indol-3-yl)ethyl)-4-(6-hydroxymethyl-1H-indol-4-yl)piperazine,
1-(2-(5-Bromo-1H-indol-3-yl)ethyl)-4-(6-hydroxymethyl-1H-indol-4-yl)piperazine,
1-(3-(6-Fluoro-1,2-benzisoxazol-3-yl)-4-propyl)-4-(1H-indol-4-yl)piperazine,
1-(2-(1H-Indol-3-yl) ethyl)-4-(6-methoxycarbonyl-1H-indol-4-yl)piperazine,
1-(2-(6-Chloro-1H-indol-3-yl)ethyl)-4-(6-methoxycarbonyl-1H-indol-4-yl)piperazine,
1-(2-(5-Fluoro-3-benzofuranyl)ethyl)-4-(6-methoxycarbonyl-1H-indol-4-yl)piperazine,
1-(5-Fluoro-3-benzofuranylmethyl)-4-(1H-indol-4-yl)piperazine,
1-(3-Cyano-1H-indol-4-yl)-4-(2-(1H-indol-3-yl)ethyl)piperazine,
1-(3-Cyano-1H-indol-4-yl)-4-(2-(5-fluoro-3-benzofuranyl)ethyl)piperazine, 1-(2-(6-Chloro-1H-indol-3-yl)ethyl)-4-(3-cyano-1H-indol-4-yl)piperazine, 1-(2-(3-Benzofuranyl)ethyl)-4-(3-cyano-1H-indol-4-yl)piperazine, 1-(1H-Indol-4-yl)-4-(2-(5-methyl-3-benzofuranyl)ethyl)piperazine, 1-(1H-Indol-4-yl)-4-(2-(4-methyl-3-benzofuranyl)ethyl)piperazine, 1-(2-(5-Chloro-3-benzofuranyl)ethyl)-4-(1H-indol-4-yl)piperazine, 1-(1H-Indol-4-yl)-4-(2-(6-methyl-3-benzofuranyl)ethyl)piperazine, 1-(2-(7-Chloro-3-benzofuranyl)ethyl)-4-(1H-indol-4-yl)piperazine, 1-(2-(4-Chloro-1H-indol-3-yl)ethyl)-4-(3-cyano-1H-indol-4-yl)piperazine, 1-(2-(5-Chloro-1H-indol-3-yl)ethyl)-4-(1H-indol-4-yl)piperazine, 1-(2-(7-Bromo-1H-indol-3-yl)ethyl)-4-(1H-indol-4-yl)piperazine, 1-(2-(4-Chloro-1H-indol-3-yl)ethyl)-4-(1H-indol-4-yl)piperazine, 1-(2-(6-Trifluoromethyl-1H-indol-3-yl)ethyl)-4-(1H-indol-4-yl)piperazine, 1-(1H-Indol-4-yl)-4-(2-(5-methyl-1H-indol-3-yl)ethyl)piperazine, 1-(1H-Indol-4-yl)-4-(2-(6-methyl-1H-indol-3-yl)ethyl)piperazine, 1-(1H-Indol-4-yl)-4-(2-(7-methyl-1H-indol-3-yl)ethyl)piperazine, 1-(2-(4,5-Dichloro-3-benzofuranyl)ethyl)-4-(1H-indol-4-yl)piperazine, 1-(2-(5-Bromo-3-benzofuranyl)ethyl)-4-(1H-indol-4-yl)piperazine, 1-(1H-Indol-4-yl)-4-(3-(4-methyl-3-benzofuranyl)-1-propyl)piperazine, 1-(3-(4-Chloro-3-benzofuranyl)-1-propyl)-4-(1H-indol-4-yl)piperazine, 1-(2-(6-Chloro-1H-indol-3-yl)ethyl)-4-(6-chloro-1H-indol-4-yl)piperazine, 1-(2-(6-Chloro-1H-indol-3-yl)ethyl)-4-(6-fluoro-1H-indol-4-yl)piperazine, 1-(2-(6-Chloro-1H-indol-3-yl)ethyl)-4-(6-cyano-1H-indol-4-yl)piperazine, 1-(2-(6-Chloro-1H-indol-3-yl)ethyl)-4-(7-chloro-1H-indol-4-yl)piperazine, 1-(2-(6-Chloro-1H-indol-3-yl)ethyl)-4-(7-cyano-1H-indol-4-yl)piperazine, 1-(2-(6-Chloro-1H-indol-3-yl)ethyl)-4-(2-cyano-1H-indol-4-yl)piperazine, 1-(2-(6-Chloro-1H-indol-3-yl)ethyl)-4-(1H-indolin-4-yl)piperazine, 1-(2-(6-Chloro-1H-indol-3-yl)ethyl)-4-(1H-indol-6-yl)piperazine and 1-(2-(6-Chloro-1H-indol-3-yl)ethyl)-4-(1H-indol-7-yl)piperazine or a pharmaceutically acceptable acid addition salt thereof.

12. A pharmaceutical composition comprising a compound according to claim 1 or a pharmaceutically acceptable acid addition salt thereof and at least one pharmaceutically acceptable carrier or diluent.

13. A method for the treatment of a disorder or disease of living animal body, including a human, which is responsive to the inhibition of serotonin reuptake and antagonism of 5-HT$_{1A}$ receptors comprising administering to such a living animal body, including a human, a therapeutically effective amount of a compound according to claim 1 or a pharmaceutically acceptable acid addition salt thereof.

14. A method for the treatment of an affective disorder, including depression psychosis, anxiety disorders including general anxiety disorder and panic disorder and obsessive compulsive disorder in a living animal body, including a human, comprising administering a therapeutically effective amount of a compound according to claim 1 or a pharmaceutically acceptable acid addition salt thereof.

* * * * *

UNITED STATES PATENT AND TRADEMARK OFFICE
CERTIFICATE OF CORRECTION

PATENT NO. : 6,391,882 B1
DATED : May 21 2002
INVENTOR(S) : Ejner Knud Moltzen and Ivan Mikkelsen and Christian Krog-Jensen It is certified that error appears in the above-identified patent and that said Letters Patent is hereby corrected as shown below:

<u>Title page,</u>
Item [75], Inventors, please change the 3$^{rd}$ inventor to correct his name from:
"Christian Korg-Jensen," to -- Christian Krog-Jensen --.

Item [86], PCT No. :, the § 371 Date and § 102(e) Date: change from:
"§ 371 Date: Feb. 1, 2001" to -- § 371 Date: Feb. 2, 2001 --.
and change
"§ 102(e) Date: Feb. 1, 2001" to -- § 102(e) Date: Feb. 2, 2001 --.

Item [87], PCT Pub. Date: please change the date from:
"Dec. 17, 1999" to -- Dec. 29, 1999 --.

Signed and Sealed this

Seventh Day of January, 2003

JAMES E. ROGAN
*Director of the United States Patent and Trademark Office*